United States Patent
Estrela Ariguel et al.

(10) Patent No.: US 11,730,751 B2
(45) Date of Patent: Aug. 22, 2023

(54) TREATING AND PREVENTING MOTOR NEURON DISEASES USING NICOTINAMIDE RIBOSIDE

(71) Applicants: Elysium Health, Inc., New York, NY (US); UNIVERSITAT DE VALÈNCIA-ESTUDI GENERAL, Valencia (ES); FUNDACIÓN UNIVERSIDAD CATÓLICA DE VALENCIA SAN VICENTE MÁRTIR, Valencia (ES)

(72) Inventors: José Maria Estrela Ariguel, Valencia (ES); José Enrique De La Rubia Orti, Valencia (ES); Ryan Dellinger, Azusa, CA (US)

(73) Assignees: UNIVERSITAT DE VALÈNCIA-ESTUDI GENERAL, Valencia (ES); FUNDACIÓN UNIVERSIDAD CATÓLICA DE VALENCIA SAN VICENTE MÁRTIR, Valencia (ES); Elysium Health, Inc., New York, NY (US)

( * ) Notice: Subject to any disclaimer, the term of this patent is extended or adjusted under 35 U.S.C. 154(b) by 390 days.

(21) Appl. No.: 16/614,244

(22) PCT Filed: May 16, 2018

(86) PCT No.: PCT/US2018/032932
§ 371 (c)(1),
(2) Date: Nov. 15, 2019

(87) PCT Pub. No.: WO2018/213420
PCT Pub. Date: Nov. 22, 2018

(65) Prior Publication Data
US 2022/0305039 A1    Sep. 29, 2022

Related U.S. Application Data

(60) Provisional application No. 62/614,003, filed on Jan. 5, 2018, provisional application No. 62/507,585, filed on May 17, 2017.

(51) Int. Cl.
*A61K 31/706* (2006.01)
*A61K 31/09* (2006.01)
*A61K 31/23* (2006.01)
*A61P 25/28* (2006.01)

(52) U.S. Cl.
CPC ............ *A61K 31/706* (2013.01); *A61K 31/09* (2013.01); *A61K 31/23* (2013.01); *A61P 25/28* (2018.01)

(58) Field of Classification Search
CPC ...... A61K 31/706; A61K 31/09; A61K 31/23; A61P 25/28
USPC .......................................................... 514/43
See application file for complete search history.

(56) References Cited

FOREIGN PATENT DOCUMENTS

| WO | WO-2007/008548 A2 | 1/2007 |
|---|---|---|
| WO | WO-2016/149277 A1 | 9/2016 |
| WO | WO-2016/200447 A1 | 12/2016 |
| WO | WO-2018/213420 A1 | 11/2018 |

OTHER PUBLICATIONS

Cuzzola et al., "Role of Resveratrol and its Analogues in the Treatment of Neurodegenerative Diseases: Focus on Recent Discoveries," CNS and Neurological Disorders—Drug Targets, 10(7): 849-862 (2011).
Extended European Search Report for EP Application No. 18803104.1 dated Jan. 28. 2021.
Harlan et al., "Enhancing NAD+ Salvage Pathway Reverts the Toxicity of Primary Astrocytes Expressing Amyotrophic Lateral Sclerosis-linked Mutant Superoxide Dismutase 1 (SOD1)," Journal of Biological Chemistry, 291(20): 10836-10846 (2016).
Alsuntangled Group, "ALSUntangled 15: Coconut Oil," Amyotrophic Lateral Sclerosis, 12: 328-330 (2012).
International Search Report and Written Opinion for International Application No. PCT/US18/32932 dated Aug. 1, 2018.

*Primary Examiner* — Kristin A Vajda
(74) *Attorney, Agent, or Firm* — Foley Hoag LLP; Brendan T. Jones; Allison L. Gilder

(57) ABSTRACT

Provided herein are methods and compositions related to treating motor neuron diseases, such as ALS, in a subject by administering to the subject (e.g., orally administering to the subject) a composition comprising nicotinamide riboside and/or pterostilbene.

20 Claims, 9 Drawing Sheets

Survival mice number/week

| Week | WT | SOD1 | SOD1 (+NR) | SOD1 (+PT) | SOD1 (+NR+PT) | SOD1 (+R) | SOD1 (+NR+R) |
|---|---|---|---|---|---|---|---|
| 8 | 12 | 12 | 12 | 12 | 12 | 12 | 12 |
| 9 | 12 | 12 | 12 | 12 | 12 | 12 | 12 |
| 10 | 12 | 12 | 12 | 12 | 12 | 12 | 12 |
| 11 | 12 | 12 | 12 | 12 | 12 | 12 | 12 |
| 12 | 12 | 12 | 12 | 12 | 12 | 12 | 12 |
| 13 | 12 | 12 | 12 | 12 | 12 | 12 | 12 |
| 14 | 12 | 12 | 12 | 12 | 12 | 12 | 12 |
| 15 | 12 | 12 | 12 | 12 | 12 | 12 | 12 |
| 16 | 12 | 12 | 12 | 12 | 12 | 12 | 12 |
| 17 | 12 | 11 | 12 | 11 | 12 | 10 | 11 |
| 18 | 12 | 10 | 11 | 11 | 11 | 9 | 10 |
| 19 | 12 | 8 | 10 | 9 | 11 | 7 | 10 |
| 20 | 12 | 4 | 7 | 7 | 10 | 5 | 9 |
| 21 | 12 | 0 | 2 | 0 | 8 | 0 | 6 |
| 22 | 12 | 0 | 0 | 0 | 6 | 0 | 1 |
| 23 | 12 | 0 | 0 | 0 | 0 | 0 | 0 |

FIG. 2

NEUROLOGICAL SCORE

| WEEK | WT | SOD1 | SOD1+NR | SOD1+PT | SOD1+NR+PT | SOD1+R | SOD1+NR+R |
|---|---|---|---|---|---|---|---|
| 8 | 0 ± 0 | 0 ± 0 | 0 ± 0 | 0 ± 0 | 0 ± 0 | 0 ± 0 | 0 ± 0 |
| 9 | 0 ± 0 | 0 ± 0 | 0 ± 0 | 0 ± 0 | 0 ± 0 | 0 ± 0 | 0 ± 0 |
| 10 | 0 ± 0 | 0 ± 0 | 0 ± 0 | 0 ± 0 | 0 ± 0 | 0 ± 0 | 0 ± 0 |
| 11 | 0 ± 0 | 0 ± 0 | 0 ± 0 | 0 ± 0 | 0 ± 0 | 0 ± 0 | 0 ± 0 |
| 12 | 0 ± 0 | 0.75 ± 0.45** | 0 ± 0++ | 0.50 ± 0.52 | 0 ± 0++ | 0.75 ± 0.45** | 0 ± 0++ |
| 13 | 0 ± 0 | 1 ± 0** | 0 ± 0++ | 1 ± 0** | 0 ± 0++ | 1 ± 0** | 0 ± 0++ |
| 14 | 0 ± 0 | 1 ± 0** | 0.33 ± 0.49++ | 1 ± 0** | 0 ± 0++ | 1.08 ± 0.29** | 0.25 ± 0.45++ |
| 15 | 0 ± 0 | 1 ± 0** | 0.75 ± 0.45** | 1 ± 0** | 0 ± 0++aa | 1.08 ± 0.29** | 0.83 ± 0.39** |
| 16 | 0 ± 0 | 1.42 ± 0.51** | 0.92 ± 0.29** | 1.75 ± 0.45** | 0.42 ± 0.51+ | 1.83 ± 0.39** | 1 ± 0** |
| 17 | 0 ± 0 | 1.64 ± 0.50 | 1.42 ± 0.51 | 1.91 ± 0.30 | 0.92 ± 0.29a | 2 ± 0 | 1.45 ± 0.52 |
| 18 | 0 ± 0 | 2.30 ± 0.48** | 2 ± 0** | 2 ± 0** | 1 ± 0**++aa | 2.89 ± 0.33** | 2 ± 0** |
| 19 | 0 ± 0 | 3 ± 0** | 2.55 ± 0.52** | 2.89 ± 0.33** | 1.82 ± 0.40**++ | 3 ± 0** | 2.70 ± 0.48** |
| 20 | 0 ± 0 | 4 ± 0** | 3.40 ± 0.52** | 4 ± 0** | 2.40 ± 0.52**+a | 4 ± 0** | 3.56 ± 0.53** |

FIG. 3

TAIL ELEVATION

| WEEK | WT | SOD1 | SOD1+NR | SOD1+PT | SOD1+NR+PT | SOD1+R | SOD1+NR+R |
|------|-----|----------|----------|----------|----------|----------|----------|
| 8  | 0 ± 0 | 0 ± 0 | 0 ± 0 | 0 ± 0 | 0 ± 0 | 0 ± 0 | 0 ± 0 |
| 9  | 0 ± 0 | 0 ± 0 | 0 ± 0 | 0 ± 0 | 0 ± 0 | 0 ± 0 | 0 ± 0 |
| 10 | 0 ± 0 | 0 ± 0 | 0 ± 0 | 0 ± 0 | 0 ± 0 | 0 ± 0 | 0 ± 0 |
| 11 | 0 ± 0 | 0.2 ± 0.4 | 0 ± 0 | 0 ± 0 | 0 ± 0 | 0 ± 0 | 0 ± 0 |
| 12 | 0 ± 0 | 0.8 ± 0.5** | 0 ± 0† | 0.5 ± 0.5 | 0 ± 0† | 0.6 ± 0.5* | 0 ± 0† |
| 13 | 0 ± 0 | 0.9 ± 0.3** | 0 ± 0†† | 0.9 ± 0.3** | 0 ± 0†† | 1 ± 0** | 0 ± 0†† |
| 14 | 0 ± 0 | 1 ± 0** | 0.3 ± 0.5† | 1 ± 0** | 0 ± 0†† | 1 ± 0** | 0.5 ± 0.5† |
| 15 | 0 ± 0 | 1.2 ± 0.4** | 0.7 ± 0.5** | 1.1 ± 0.3** | 0.2 ± 0.4†† | 1.3 ± 0.5** | 1 ± 0** |
| 16 | 0 ± 0 | 1.3 ± 0.5** | 1 ± 0** | 1.8 ± 0.6** | 0.8 ± 0.4** | 1.8 ± 0.4** | 1.2 ± 0.4** |
| 17 | 0 ± 0 | 1.8 ± 0.6** | 1.3 ± 0.5** | 2 ± 0** | 1 ± 0***† | 2 ± 0** | 2 ± 0.4** |
| 18 | 0 ± 0 | 2.1 ± 0.3** | 1.8 ± 0.5** | 2.1 ± 0.3** | 1.2 ± 0.4**†† | 2.3 ± 0.5** | 2.1 ± 0.3** |
| 19 | 0 ± 0 | 2.3 ± 0.5** | 2 ± 0** | 2.1 ± 0.3** | 1.8 ± 0.4** | 2.3 ± 0.5** | 2 ± 0** |
| 20 | 0 ± 0 | 3 ± 0** | 2.8 ± 0.4** | 3 ± 0** | 2.7 ± 0.5** | 3 ± 0** | 2.8 ± 0.4** |

FIG. 4

ROTAROD

| WEEK | WT | SOD1 | SOD1+NR | SOD1+PT | SOD1+NR+PT | SOD1+R | SOD1+NR+R |
|---|---|---|---|---|---|---|---|
| 8  | 1200 ± 0 | 1136 ± 124 | 1200 ± 0 | 1200 ± 0 | 1200 ± 0 | 1200 ± 0 | 1200 ± 0 |
| 9  | 1200 ± 0 | 1200 ± 0 | 1200 ± 0 | 1200 ± 0 | 1200 ± 0 | 1200 ± 0 | 1200 ± 0 |
| 10 | 1200 ± 0 | 1200 ± 0 | 1200 ± 0 | 1200 ± 0 | 1200 ± 0 | 1200 ± 0 | 1200 ± 0 |
| 11 | 1200 ± 0 | 1087 ± 170 | 1200 ± 0 | 1091 ± 136 | 1200 ± 0 | 1108 ± 119 | 1200 ± 0 |
| 12 | 1200 ± 0 | 966 ± 139** | 1200 ± 0$^{++}$ | 968 ± 113** | 1200 ± 0$^{++}$ | 1012 ± 136* | 1200 ± 0$^{++}$ |
| 13 | 1200 ± 0 | 885 ± 129** | 1088 ± 133 | 885 ± 45** | 1200 ± 0$^{++}$ | 857 ± 98** | 1159 ± 90$^{++}$ |
| 14 | 1200 ± 0 | 774 ± 87** | 1105 ± 121$^{++}$ | 794 ± 95** | 1200 ± 0$^{++}$ | 736 ± 135** | 1021 ± 129*$^{++}$ |
| 15 | 1200 ± 0 | 670 ± 92** | 1051 ± 138$^{++}$ | 731 ± 78** | 1200 ± 0$^{++a}$ | 640 ± 127** | 859 ± 112** |
| 16 | 1200 ± 0 | 447 ± 119** | 809 ± 148**$^{++}$ | 392 ± 115** | 1106 ± 135$^{++a}$ | 384 ± 201** | 763 ± 57**$^{++}$ |
| 17 | 1200 ± 0 | 268 ± 118** | 446 ± 158** | 228 ± 99** | 1021 ± 106***$^{++aa}$ | 210 ± 69** | 498 ± 176** |
| 18 | 1200 ± 0 | 134 ± 81** | 234 ± 49** | 157 ± 53** | 934 ± 100**$^{++aa}$ | 66 ± 121** | 216 ± 70** |
| 19 | 1200 ± 0 | 23 ± 20** | 97 ± 83** | 28 ± 30** | 438 ± 257**$^{++aa}$ | 19 ± 7** | 64 ± 75** |
| 20 | 1200 ± 0 | 0 ± 0** | 13 ± 12** | 0 ± 0** | 189 ± 162**$^{+aa}$ | 0 ± 0** | 7 ± 9** |

FIG. 5

HANGING WIRE

| WEEK | WT | SOD1 | SOD1+NR | SOD1+PT | SOD1+NR+PT | SOD1+R | SOD1+NR+R |
|---|---|---|---|---|---|---|---|
| 8  | 171 ± 13 | 175 ± 9    | 180 ± 0       | 180 ± 0       | 180 ± 0              | 180 ± 0       | 180 ± 0 |
| 9  | 178 ± 5  | 177 ± 6    | 180 ± 0       | 180 ± 0       | 180 ± 0              | 180 ± 0       | 180 ± 0 |
| 10 | 175 ± 11 | 177 ± 5    | 180 ± 0       | 180 ± 0       | 180 ± 0              | 180 ± 0       | 180 ± 0 |
| 11 | 177 ± 11 | 177 ± 7    | 180 ± 0       | 173 ± 10      | 180 ± 0              | 175 ± 6       | 180 ± 0 |
| 12 | 178 ± 5  | 153 ± 24   | 180 ± 0+      | 166 ± 10      | 180 ± 0+             | 168 ± 10      | 180 ± 0+ |
| 13 | 179 ± 3  | 128 ± 27** | 175 ± 8++     | 159 ± 9**     | 180 ± 0++            | 148 ± 12**    | 172 ± 12++ |
| 14 | 180 ± 0  | 99 ± 25**  | 172 ± 11++    | 127 ± 14**    | 180 ± 0++            | 124 ± 12**    | 164 ± 11*++ |
| 15 | 178 ± 6  | 75 ± 17**  | 159 ± 12**++  | 113 ± 17**+   | 171 ± 11++           | 78 ± 24**     | 124 ± 25**++ |
| 16 | 176 ± 7  | 45 ± 12**  | 145 ± 16**++  | 103 ± 16**++  | 161 ± 12**++         | 38 ± 19**     | 72 ± 16**+ |
| 17 | 173 ± 9  | 29 ± 11**  | 60 ± 17**+    | 28 ± 13**     | 146 ± 13***++aa      | 19 ± 7**      | 49 ± 20** |
| 18 | 170 ± 13 | 18 ± 11**  | 27 ± 8**      | 17 ± 8**      | 63 ± 9**++aa         | 7 ± 7**       | 22 ± 6** |
| 19 | 176 ± 7  | 2 ± 4**    | 12 ± 7**      | 3 ± 4**       | 39 ± 11**++aa        | 2 ± 4**       | 6 ± 9** |
| 20 | 175 ± 8  | 0 ± 0**    | 1 ± 3**       | 0 ± 0**       | 18 ± 16***           | 0 ± 0**       | 0.6 ± 1** |

FIG. 6

TREADMILL

| WEEK | WT | SOD1 | SOD1+NR | SOD1+PT | SOD1+NR+PT | SOD1+R | SOD1+NR+R |
|------|-----|------|---------|---------|------------|--------|-----------|
| 8 | 81.1 ± 20.9 | 82.3 ± 17.6 | 62.8 ± 29.0 | 67.1 ± 27.0 | 64.5 ± 31.1 | 81.8 ± 18.3 | 80.2 ± 20.7 |
| 9 | 86.2 ± 13.1 | 86.2 ± 13.3 | 60.2 ± 31.2 | 57.4 ± 29.0 | 81.1 ± 20.8 | 85.9 ± 13.7 | 81.7 ± 18.1 |
| 10 | 81.0 ± 21.2 | 85.9 ± 13.0 | 90.0 ± 0.0 | 90.0 ± 0.0 | 86.2 ± 13.0 | 90.0 ± 0.0 | 90.0 ± 0.0 |
| 11 | 76.4 ± 24.8 | 79.8 ± 23.9 | 90.0 ± 0.0 | 86.3 ± 13.0 | 78.8 ± 20.6 | 90.0 ± 0.0 | 68.3 ± 27.3 |
| 12 | 68.4 ± 26.9 | 80.4 ± 22.6 | 86.2 ± 13.1 | 81.8 ± 18.2 | 76.8 ± 23.5 | 76.8 ± 20.8 | 84.8 ± 17.9 |
| 13 | 72.1 ± 26.6 | 61.5 ± 26.0 | 82.4 ± 17.7 | 64.2 ± 27.5 | 85.8 ± 13.2 | 80.2 ± 21.2 | 75.9 ± 25.8 |
| 14 | 61.1 ± 31.0 | 60.7 ± 25.9 | 70.2 ± 29.7 | 82.4 ± 17.7 | 81.9 ± 18.5 | 70.0 ± 27.2 | 81.6 ± 18.1 |
| 15 | 78.3 ± 27.4 | 52.5 ± 33.9 | 74.0 ± 28.8 | 75.5 ± 24.5 | 82.0 ± 18.2 | 74.5 ± 26.3 | 79.1 ± 20.8 |
| 16 | 82.1 ± 17.8 | 21.2 ± 22.2** | 63.2 ± 28.6 | 21.0 ± 24.5** | 63.7 ± 27.6 | 11.6 ± 5.4** | 70.8 ± 24.0++ |
| 17 | 90.0 ± 0.0 | 11.2 ± 3.3*** | 40.3 ± 31.3** | 8.5 ± 3.3*** | 57.1 ± 27.6*+++ | 6.9 ± 1.8*** | 46.4 ± 33.0*** |
| 18 | 77.2 ± 23.1 | 5.4 ± 3.2*** | 8.4 ± 2.5** | 5.2 ± 2.2*** | 26.8 ± 12.1***+aa | 0.9 ± 1.5***+ | 16.3 ± 18.0** |
| 19 | 89.8 ± 0.6 | 0.1 ± 0.2** | 2.4 ± 2.6** | 0.6 ± 0.9*** | 8.0 ± 4.4***+a | 0.3 ± 0.2** | 1.6 ± 2.0** |
| 20 | 81.0 ± 21.0 | 0.0 ± 0.0** | 0.1 ± 0.2** | 0.0 ± 0.0** | 2.4 ± 2.2** | 0.0 ± 0.0** | 0.1 ± 0.2** |

FIG. 7

ACTIMETER

| PERIOD | | WT | SOD1 | SOD1+NR | SOD1+PT | SOD1+NR+PT | SOD1+R | SOD1+NR+R |
|---|---|---|---|---|---|---|---|---|
| I (weeks 8-11) | MS | 1328 ± 162 | 1263 ± 126 | 1341 ± 143 | 1285 ± 112 | 1378 ± 148 | 1175 ± 177 | 1349 ± 135 |
|  | MF | 63 ± 21 | 52 ± 25 | 66 ± 23 | 62 ± 30 | 74 ± 26 | 69 ± 19 | 69 ± 25 |
| II (weeks 12-15) | MS | 1436 ± 104 | 1217 ± 144 | 1417 ± 94 | 1305 ± 126 | 1415 ± 92 | 1246 ± 83* | 1418 ± 41+ |
|  | MF | 93 ± 20 | 59 ± 20 | 88 ± 32 | 72 ± 21 | 83 ± 31 | 59 ± 18 | 66 ± 22 |
| III (weeks 16-18) | MS | 1460 ± 176 | 345 ± 90** | 656 ± 99**++ | 397 ± 75** | 881 ± 101***+++aa | 288 ± 72** | 654 ± 92***++ |
|  | MF | 97 ± 28 | 21 ± 5** | 50 ± 27* | 30 ± 16** | 53 ± 20*+ | 24 ± 10** | 40 ± 14***+ |
| IV (weeks 19-20) | MS | 1216 ± 159 | 123 ± 59 | 73 ± 30 | 51 ± 20* | 164 ± 72a | 58 ± 25 | 77 ± 33 |
|  | MF | 62 ± 21 | 1 ± 2** | 3 ± 4** | 1 ± 2** | 9 ± 5*** | 0 ± 0** | 1 ± 2** |

FIG. 8

ELECTROPHYSIOLOGICAL PARAMETERS

| Group | Amplitude (mV) | | Latency (ms) | | Nerve conduction velocity (m/s) | |
|---|---|---|---|---|---|---|
| | W8 | W18 | W8 | W18 | W8 | W18 |
| WT | 2.45 ± 0.37 | 2.55 ± 0.38 | 0.32 ± 0.09 | 0.15 ± 0.10* | 6.80 ± 0.42 | 6.30 ± 0.26 |
| SOD1 | 1.45 ± 0.48* | 0.65 ± 0.24** | 0.72 ± 0.12** | 1.47 ± 0.22** | 3.42 ± 0.43** | 1.85 ± 0.31** |
| SOD1+NR | 2.37 ± 0.30⁺⁺ | 1.66 ± 0.25*⁺⁺ | 0.27 ± 0.05⁺⁺ | 0.15 ± 0.06⁺⁺ | 5.65 ± 0.55*⁺⁺ | 3.92 ± 0.97***⁺⁺ |
| SOD1+PT | 1.47 ± 0.25** | 0.60 ± 0.18***⁺ | 0.65 ± 0.19*⁺⁺ | 1.20 ± 0.22***⁺ | 3.20 ± 0.18***⁺⁺ | 1.85 ± 0.31** |
| SOD1+NR+PT | 2.75 ± 0.13⁺⁺ | 1.85 ± 0.13**⁺⁺ | 0.25 ± 0.06⁺⁺ | 0.12 ± 0.05⁺⁺⁺ | 6.17 ± 0.74⁺⁺ | 4.87 ± 0.38***⁺⁺ |
| SOD1+R | 1.37 ± 0.26** | 0.57 ± 0.22***⁺⁺ | 0.60 ± 0.08***⁺⁺ | 1.10 ± 0.14***⁺⁺ | 3.10 ± 0.18***⁺⁺ | 1.75 ± 0.13** |
| SOD1+NR+R | 2.30 ± 0.27⁺ | 1.67 ± 0.09***⁺⁺ | 0.20 ± 0.08⁺⁺ | 0.22 ± 0.12⁺⁺ | 5.10 ± 0.63***⁺⁺ | 3.77 ± 1.29***⁺⁺ |

FIG. 9

TREATING AND PREVENTING MOTOR NEURON DISEASES USING NICOTINAMIDE RIBOSIDE

CROSS-REFERENCE TO RELATED APPLICATIONS

This application is a § 371 national-stage application based on PCT/US18/32932, filed May 16, 2018 which claims the benefit of U.S. Provisional Application No. 62/507,585, filed on May 17, 2017, and U.S. Provisional Application No. 62/614,003, filed on Jan. 5, 2018 each of which is hereby incorporated herein in their entirety by this reference.

BACKGROUND

Amyotrophic lateral sclerosis (ALS) is a progressive degenerative disease of the voluntary motor system characterized by stiff muscles, muscle twitching, and gradually worsening weakness due to muscles decreasing in size. Disease progression results in difficulty speaking, swallowing, and breathing, eventually leading to respiratory failure and death in most effected patients. The average survival from onset to death is two to four years. To date, no cure and few therapies have been developed for ALS. Accordingly, there is a great need for new compositions and methods for the treatment of ALS and other motor neuron diseases.

SUMMARY

According to certain aspects, provided herein are methods and compositions related to treating motor neuron diseases (e.g., amyotrophic lateral sclerosis, or ALS) in a subject by administering to the subject (e.g., orally administering to the subject) a composition comprising a compound of Formula I or Formula II (e.g., nicotinamide riboside), and/or a compound of formula III (e.g., pterostilbene). In certain embodiments, the motor neuron disease is ALS, hereditary spastic paraplegia (HSP), primary lateral sclerosis (PLS), progressive muscular atrophy (PMA), progressive bulbar palsy (PBP), pseudobulbar palsy, or a spinal muscular atrophy.

In certain aspects, the methods and compositions provided herein relate to the slowing or reversing the progression of motor neuron degeneration in a subject by administering to the subject (e.g., orally administering to the subject) a composition comprising a compound of Formula I or Formula II (e.g., nicotinamide riboside), and/or a compound of Formula III (e.g., pterostilbene). In some embodiments, the subject has a motor neuron disease (e.g., ALS, HSP, PLS, PMA, PBP, pseudobulbar palsy or spinal muscular atrophy).

In certain embodiments, the composition comprises a compound of Formula I or Formula II (e.g., at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg or at least 2400 mg of a compound of Formula I or Formula II). In some embodiments, the composition comprises a compound of formula III (e.g., at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg, or at least 600 mg of a compound of Formula III). In certain embodiments, the composition comprises both a compound of Formula I or Formula II (e.g., at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, or at least 2400 mg of a compound of Formula I or Formula II) and a compound of Formula III (e.g., at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg, or at least 600 mg of a compound of Formula III).

In certain embodiments, the method comprises administering a plurality of doses of the composition. In some embodiments, at least 7 doses of the composition are administered. In some embodiments, at least 30 doses of the composition are administered. In some embodiments, at least 60 or more doses of the composition are administered. In some embodiments, each dose comprises at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, or at least 2400 mg of a compound of Formula I or Formula II (e.g., nicotinamide riboside). In some embodiments, each dose comprises at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg or at least 600 mg of a compound of Formula III (e.g., pterostilbene).

In certain embodiments, each dose comprises at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg or at least 2400 mg of a compound of Formula I or Formula II (e.g., nicotinamide riboside) and at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg or at least 600 mg of a compound of Formula III (e.g., pterostilbene).

In certain embodiments, a dose of the composition is administered at regular intervals over a period of time. In some embodiments, a dose of the composition is administered at least once a week. In some embodiments, a dose of the composition is administered at least twice a week. In certain embodiments, a dose of the composition is administered at least three times a week. In some embodiments, a dose of the composition is administered at least once a day. In some embodiments, a dose of the composition is administered at least twice a day. In some embodiments, doses of the composition are administered for at least 1 week, for at least 2 weeks, for at least 3 weeks, for at least 4 weeks, for at least 1 month, for at least 2 months, for at least 3 months, for at least 4 months, for at least 5 months, for at least 6 months or for at least 1 year.

In some embodiments, the subject is given a motor function test and/or a cognition and conduct function test. The motor function test may be Revised Amyotrophic Lateral Sclerosis Functional Rating Scale (ALSFRS-R). The cognition and conduct test may be Complutense Verbal Learning Test (TAVEC), Symbol Digit Modalities Test (SDMT), Verbal Fluency Test, Digit Span (Wechsler Memory Scale III), D2 Attention Test, Wechsler Memory Scale III for Letters and Numbers, London Tower Test, Stroop test, Frontal System Behavior Scale (FrSBe), or Brief Test (subjective conduct).

In some embodiments, the method further comprises measuring a feature (e.g., a feature associated with inflammation) in the subject. Examples of features that may be tested are the level of a cytokine, level of amyloid A protein, level of macrophage activation marker neopterin, level of creatine phosphokinase (CPK), level of erythrocyte sedimentation rate, level of C-reactive protein, plasma viscosity, and/or white blood cell count.

In some embodiments, the method further comprises administering a fatty acid supplement (e.g., coconut oil) to the subject.

In certain embodiments, the composition is formulated for oral delivery. In some embodiments, the composition is formulated as a pill, a tablet, or a capsule. In some embodiments, the composition is administered orally. In certain embodiments, the composition is self-administered.

BRIEF DESCRIPTION OF THE DRAWINGS

FIG. 2 shows the number of survival mice at each week for different treatment groups of mice.

FIG. 3 shows the neurological scores of different treatment groups of mice at each week.

FIG. 4 shows the results of the tail elevation test of different treatment groups of mice at each week.

FIG. 5 shows the results of the rotarod test of different treatment groups of mice at each week.

FIG. 6 shows the results of the hanging wire test of different treatment groups of mice at each week.

FIG. 7 shows the results of the inclined plane test of different treatment groups of mice at each week.

FIG. 8 shows the results of the motor activity by automatic evaluation of different treatment groups of mice at each period.

FIG. 9 shows the results of the electrophysiological measurements of different treatment groups of mice at week 8 and week 18.

DETAILED DESCRIPTION

General

Figure 1:
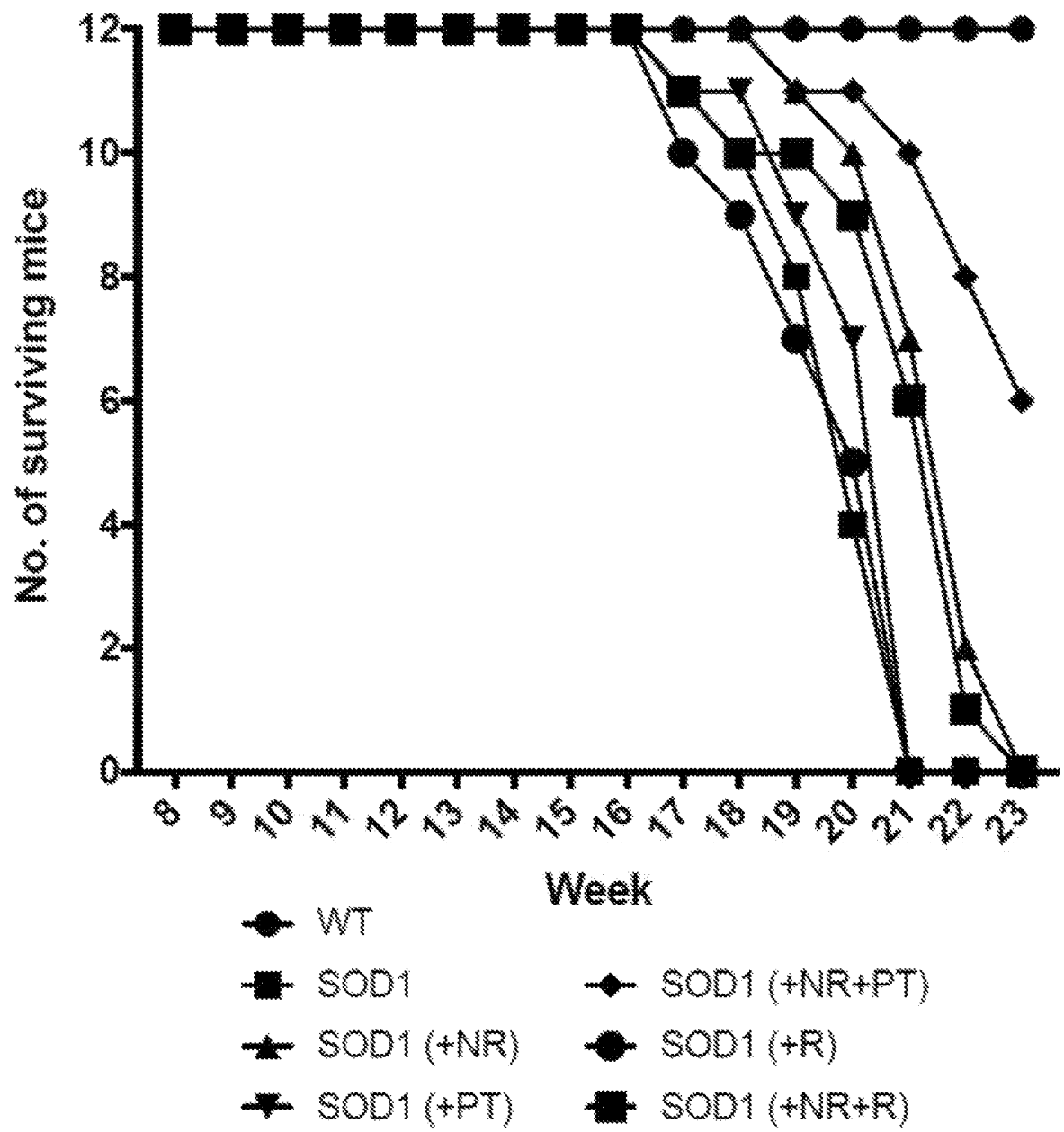
FIG. 1 shows Kaplan—Meier curves comparing survival time between groups of mice. WT, wild type B6SJLF1/J mice; SOD1, transgenic SOD1 G93A mice; NR, mice treated with nicotinamide riboside; PT, mice treated with pterostilbene; R, mice treated with resveratrol.

Provided herein are methods and compositions related to treating and/or preventing motor neuron diseases and disorders (e.g., ALS) and/or for slowing or reversing motor neuron degeneration by administering to the subject (e.g., a subject with ALS) a composition comprising a compound of Formula I or Formula II (e.g., nicotinamide riboside) and/or a compound of Formula III (e.g., pterostilbene).

Definitions

For convenience, certain terms employed in the specification, examples, and appended claims are collected here.

The articles "a" and "an" are used herein to refer to one or to more than one (i.e., to at least one) of the grammatical object of the article. By way of example, "an element" means one element or more than one element.

As used herein, the term "administering" means providing a pharmaceutical agent or composition to a subject, and includes, but is not limited to, administering by a medical professional and self-administering. Administration of a substance, a compound or an agent to a subject can be carried out using one of a variety of methods known to those skilled in the art. For example, a compound or an agent can be administered, intravenously, arterially, intradermally, intramuscularly, intraperitoneally, subcutaneously, ocularly, sublingually, orally (by ingestion), intranasally (by inhalation), intraspinally, intracerebrally, and transdermally (by absorption, e.g., through a skin duct). A compound or agent can also appropriately be introduced by rechargeable or biodegradable polymeric devices or other devices, e.g., patches and pumps, or formulations, which provide for the extended, slow or controlled release of the compound or agent. Administering can also be performed, for example, once, a plurality of times, and/or over one or more extended periods.

Appropriate methods of administering a substance, a compound or an agent to a subject will also depend, for example, on the age and/or the physical condition of the subject and the chemical and biological properties of the compound or agent (e.g., solubility, digestibility, bioavailability, stability and toxicity). In some embodiments, a compound or an agent is administered orally, e.g., to a subject by ingestion. In some embodiments, the orally administered compound or agent is in an extended release or slow release formulation, or administered using a device for such slow or extended release.

The phrase "pharmaceutically-acceptable carrier" as used herein means a pharmaceutically-acceptable material, composition or vehicle, such as a liquid or solid filler, diluent, excipient, or solvent encapsulating material.

As used herein, the term "subject" means a human or non-human animal selected for treatment or therapy.

The phrases "therapeutically-effective amount" and "effective amount" as used herein means the amount of an agent which is effective for producing the desired therapeutic effect in at least a sub-population of cells in a subject at a reasonable benefit/risk ratio applicable to any medical treatment.

"Treating" a disease in a subject or "treating" a subject having a disease refers to subjecting the subject to a pharmaceutical treatment, e.g., the administration of a drug, such that at least one symptom of the disease is decreased or prevented from worsening.

Compositions

Provided herein are pharmaceutical compositions comprising a compound of Formula I or Formula II (e.g., nicotinamide riboside) and/or a compound of formula III (e.g., pterostilbene).

Nicotinamide riboside is a pyridine-nucleoside form of niacin (i.e., vitamin $B_3$) that serves as a precursor to nicotinamide adenine dinucleotide ($NAD^+$). As used herein, "nicotinamide riboside" also includes nicotinamide riboside salts, such as nicotinamide riboside chloride. The chemical structure of nicotinamide riboside is provided below:

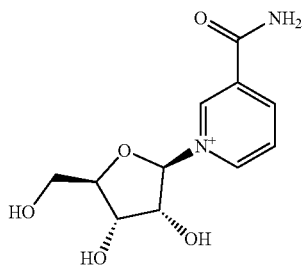 [SMILES: NC(=O)c1ccc[n+]([C@@H]2O[C@H](CO)[C@@H](O)[C@H]2O)c1]

In some embodiments, provided herein are pharmaceutical compositions comprising a compound represented by Formula (I) or a pharmaceutically acceptable salt thereof:

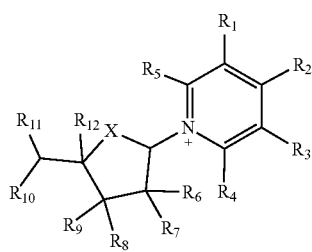

(I)

wherein, independently for each occurrence:

$R_1$, and $R_3$ are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;

$R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;

$R_6$, $R_8$, $R_{11}$, and $R_{12}$ are selected from hydrogen, ($C_1$-$C_6$)alkyl, —(($C_1$-$C_6$)alkylene)$N(R_{14})_m$, —C(O)(($C_1$-$C_6$)alkylene)$N(R_{14})_m$, cycloalkyl, heterocycloalkyl, aryl, heteroaryl, aralkyl, heteroaralkyl, —$OR_{14}$, and —$N(R_{14})_m$;

$R_7$, $R_9$, and $R_{10}$ are selected from —(($C_1$-$C_6$)alkylene)N$(R_{14})_m$, —$OR_{14}$, and —$N(R_{14})_m$;

$R_{13}$ is selected from —$OR_{14}$, —$N(R_{14})_m$, —C(O)($R_{14}$), —C(O)(O$R_{14}$), —C(O)N$(R_{14})_m$, —S(O)$_2$(O$R_{14}$), —S(O)O$R_{14}$, and —S(O)$_2$N$(R_{14})_m$;

$R_{14}$ is selected from hydrogen, ($C_1$-$C_6$)alkyl, cycloalkyl, heterocycloalkyl, aryl, heteroaryl, aralkyl, and heteroaralkyl; and X is O, S, or N($R_{14}$);

m is 2 or 3;

provided that at least one of $R_1$, $R_2$, and $R_3$ is $R_{13}$.

In some embodiments, $R_1$ is $R_{13}$. In some embodiments, $R_2$ is $R_{13}$. In some embodiments, $R_3$ is $R_{13}$.

In some embodiments, $R_{13}$ is selected from —$OR_{14}$, —$N(R_{14})_m$, —C(O)($R_{14}$), —C(O)(O$R_{14}$), and —C(O)N$(R_{14})_m$. In some embodiments, $R_{13}$ is selected from —C(O)($R_{14}$), —C(O)(O$R_{14}$), and —C(O)N$(R_{14})_m$. In some embodiments, $R_{13}$ is —C(O)N$(R_{14})_m$.

In some embodiments, $R_7$, $R_9$, and $R_{10}$ are each independently —$OR_{14}$ or —$N(R_{14})_m$. In some embodiments, $R_7$, $R_9$, and $R_{10}$ are —$OR_{14}$.

In some embodiments, the compound of formula (I) is represented by Formula (II) or a pharmaceutically acceptable salt thereof:

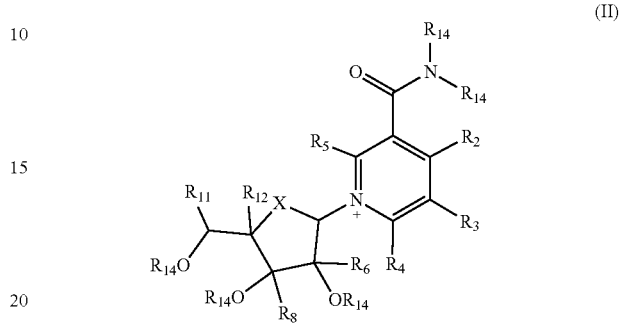

(II)

wherein, independently for each occurrence:

$R_2$ and $R_3$ are selected from hydrogen, halogen, —CN, —$NO_2$, —$OR_{14}$, —$N(R_{14})_m$, —$R_{13}$, substituted or unsubstituted ($C_1$-$C_6$)alkyl, cycloalkyl, heterocycloalkyl, aryl, heteroaryl, aralkyl, and heteroaralkyl;

$R_4$ and $R_5$ are selected from hydrogen, halogen, —CN, —$NO_2$, —$OR_{14}$, —$N(R_{14})_m$, substituted or unsubstituted ($C_1$-$C_6$)alkyl, cycloalkyl, heterocycloalkyl, aryl, heteroaryl, aralkyl, and heteroaralkyl;

$R_6$, $R_8$, $R_{11}$, and $R_{12}$ are selected from hydrogen, —$OR_{14}$, —$N(R_{14})_m$, substituted or unsubstituted ($C_1$-$C_6$)alkyl, —(($C_1$-$C_6$)alkylene)$N(R_{14})_m$, —C(O)(($C_1$-$C_6$)alkylene)N$(R_{14})_m$, cycloalkyl, heterocycloalkyl, aryl, heteroaryl, aralkyl, and heteroaralkyl;

$R_{13}$ is selected from —$OR_{14}$, —$N(R_{14})_m$, —C(O)($R_{14}$), —C(O)(O$R_{14}$), —C(O)N$(R_{14})_m$, —S(O)$_2$(O$R_{14}$), —S(O)O$R_{14}$, and —S(O)$_2$N$(R_{14})_m$;

$R_{14}$ is selected from hydrogen, ($C_1$-$C_6$)alkyl, cycloalkyl, heterocycloalkyl, aryl, heteroaryl, aralkyl, and heteroaralkyl; and m is 2 or 3.

In some embodiments of the compounds of formula (I) or (II), $R_1$, $R_2$, and $R_3$ are each independently, if present, selected from hydrogen, halogen, —CN, —$NO_2$, —$N(R_{14})_m$, —$R_{13}$, and substituted or unsubstituted ($C_1$-$C_6$)alkyl. In some embodiments, $R_1$, $R_2$, and $R_3$ are each independently, if present, selected from hydrogen, —$OR_{14}$, —$N(R_{14})_m$, and unsubstituted ($C_1$-$C_6$)alkyl. In some embodiments, $R_1$, $R_2$, and $R_3$ are each independently, if present, selected from substituted or unsubstituted ($C_1$-$C_6$)alkyl, cycloalkyl, heterocycloalkyl, aryl, heteroaryl, aralkyl, and heteroaralkyl. In some embodiments, $R_1$, $R_2$, and $R_3$ are each independently, if present, hydrogen.

In some embodiments of the compounds of formula (I) or (II), $R_4$ and $R_5$ are each independently selected from hydrogen, halogen, —CN, —$NO_2$, —$OR_{14}$, —$N(R_{14})_m$, and substituted or unsubstituted ($C_1$-$C_6$)alkyl. In some embodiments, $R_4$ and $R_5$ are each independently selected from hydrogen, —$OR_{14}$, —$N(R_{14})_m$, and unsubstituted ($C_1$-$C_6$)alkyl. In some embodiments, $R_4$ and $R_5$ are each independently selected from substituted or unsubstituted ($C_1$-$C_6$)alkyl, cycloalkyl, heterocycloalkyl, aryl, heteroaryl, and heteroaralkyl. In some embodiments, $R_4$ and $R_5$ are each hydrogen.

In some embodiments of the compounds of formula (I) or (II), $R_6$, $R_8$, $R_{11}$, and $R_{12}$ are selected from hydrogen, —$OR_{14}$, —$N(R_{14})_m$, unsubstituted ($C_1$-$C_6$)alkyl, —(($C_1$-$C_6$)alkylene)$N(R_{14})_m$, —C(O)(($C_1$-$C_6$)alkylene)$N(R_{14})_m$, cycloalkyl, heterocycloalkyl, aryl, heteroaryl, aralkyl, and heteroaralkyl. In some embodiments, $R_6$, $R_8$, $R_{11}$, and $R_{12}$ are each independently selected from hydrogen, —$OR_{14}$, —$N(R_{14})_m$, unsubstituted ($C_1$-$C_6$)alkyl, —(($C_1$-$C_6$)alkylene)$N(R_{14})_m$, and —C(O)(($C_1$-$C_6$)alkylene)$N(R_{14})_m$. In some embodiments, $R_6$, $R_8$, $R_{11}$, and $R_{12}$, are each independently selected from hydrogen, —$OR_{14}$, and —$N(R_{14})_m$. In some embodiments, $R_6$, $R_8$, $R_{11}$, and $R_{12}$ are each independently selected from unsubstituted ($C_1$-$C_6$)alkyl, cycloalkyl, heterocycloalkyl, aryl, heteroaryl, aralkyl, and heteroaralkyl. In some embodiments, $R_6$, $R_8$, $R_{11}$, and $R_{12}$ are each hydrogen.

In some embodiments, $R_7$, $R_9$, and $R_{10}$ are each independently —$OR_{14}$ or —$N(R_{14})_m$. In some embodiments, $R_7$, $R_9$ and $R_{10}$ are each —$OR_{14}$. In some embodiments, $R_7$, $R_9$, and $R_{10}$ are each —OH.

In some embodiments of the compounds of formula (I) or (II), $R_{14}$ is hydrogen or ($C_1$-$C_6$)alkyl.

In some embodiments of the compounds of formula (I) or (II), X is O or $N(R_{14})$. In some embodiments, X is O.

In some embodiments of the compounds of formula (I) or (II), the compound is

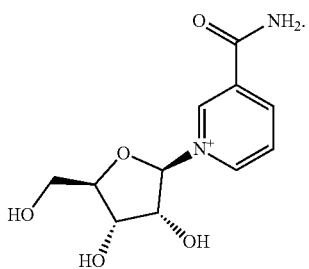

Pterostilbene is a stilbenoid and an analog of polyphenol reservatrol that has better bioavailability due to the presence of two methoxy groups that allow it to have increased lipophilic and oral absorption as well as a longer half-life due to reduced oxidation. The chemical structure of pterostilbene is provided below:

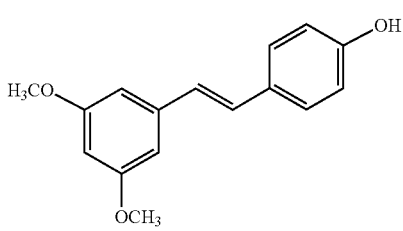 [SMILES: COc1cc(/C=C/c2ccc(O)cc2)cc(OC)c1]

In some embodiments, provided herein are pharmaceutical compositions comprising a compound represented by Formula (III) or a pharmaceutically acceptable salt thereof:

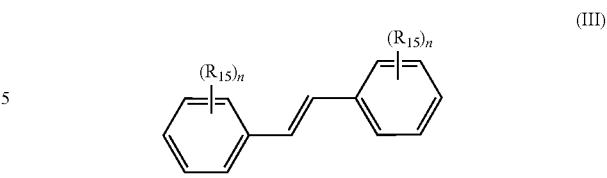

wherein, independently for each occurrence:

$R_{15}$ is selected from halogen, —CN, —$NO_2$, —$OR_{16}$, —$N(R_{16})_p$, —$S(O)_2(OR_{16})$, —$S(O)OR_{16}$, substituted or unsubstituted ($C_1$-$C_6$)alkyl, cycloalkyl, heterocycloalkyl, aryl, heteroaryl, aralkyl, and heteroaralkyl;

$R_{16}$ is selected from hydrogen, ($C_1$-$C_6$)alkyl, cycloalkyl, heterocycloalkyl, aryl, heteroaryl, aralkyl, and heteroaralkyl;

n is an integer from 0 to 5; and p is 2 or 3;

provided that at least one n is 1; and at least one $R_{15}$ is —$OR_{16}$;

provided that the compound of formula (III) is not

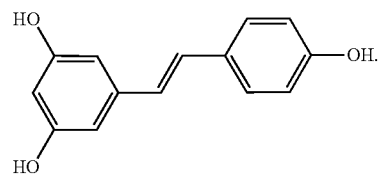 [SMILES: Oc1ccc(/C=C/c2cc(O)cc(O)c2)cc1]

In some embodiments of the compounds of formula (III), $R_{15}$ is selected from, halogen, —CN, —$NO_2$, —$OR_{16}$, —$N(R_{16})_p$, and substituted or unsubstituted ($C_1$-$C_6$)alkyl. In some embodiments, $R_{15}$ is selected from —$OR_{16}$, —$N(R_{10})_p$, and unsubstituted ($C_1$-$C_6$)alkyl. In some embodiments, $R_{15}$ is selected from substituted or unsubstituted ($C_1$-$C_6$)alkyl, cycloalkyl, heterocycloalkyl, aryl, heteroaryl, aralkyl, and heteroaralkyl. In some embodiments, $R_{15}$ is —$OR_{16}$. In some embodiments, $R_{15}$ is —$OR_{16}$; and $R_{16}$ is hydrogen or ($C_1$-$C_6$)alkyl. In some embodiments, $R_{15}$ is —$OR_{16}$; and $R_{16}$ is ($C_1$-$C_6$)alkyl, cycloalkyl, heterocycloalkyl, aryl, heteroaryl, aralkyl, and heteroaralkyl. In some embodiments, $R_{15}$ is —$OR_{16}$; and $R_{16}$ is ($C_1$-$C_6$)alkyl. In some embodiments, $R_{15}$ is —$OR_{16}$; and $R_{16}$ is ($C_1$-$C_6$)alkyl, cycloalkyl, or heterocycloalkyl.

In some embodiments, n is 1, 2, or 3. In some embodiments, n is 1 or 2.

In some embodiments, p is 2. In some embodiments, p is 3.

In one aspect, the provided herein are pharmaceutically acceptable compositions which comprise a therapeutically-effective amount of one or more of the compounds described herein (i.e., nicotinamide riboside and/or pterostilbene), formulated together with one or more pharmaceutically acceptable carriers (additives) and/or diluents. In another aspect, the agents described herein can be administered as such, or administered in mixtures with pharmaceutically acceptable carriers and can also be administered in conjunction with other agents. Conjunctive therapy thus includes sequential, simultaneous and separate, or co-administration of one or more compounds of the invention, wherein the therapeutic effects of the first administered has not entirely disappeared when the subsequent compound is administered.

As described in detail below, the pharmaceutical compositions described herein may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; or (3) sublingually.

In some embodiments, the composition comprises additional agents. For example, the composition may comprise a nutritional agent, such as an antioxidant. Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

The formulations of the compounds described herein may be presented in unit dosage form and may be prepared by any methods well known in the art of pharmacy. The amount of active ingredient which can be combined with a carrier material to produce a single dosage form will vary depending upon the host being treated and the particular mode of administration. The amount of active ingredient which can be combined with a carrier material to produce a single dosage form will generally be that amount of the agent which produces a therapeutic effect.

In certain embodiments, a formulation described herein comprises an excipient, including, but not limited to, cyclodextrins, liposomes, micelle forming agents, e.g., bile acids, and polymeric carriers, e.g., polyesters and polyanhydrides; and an agent of the invention. In some embodiments, an aforementioned formulation renders orally bioavailable an agent of the invention. Methods of preparing these formulations or compositions may include the step of bringing into association a compound of the invention with the carrier and, optionally, one or more accessory ingredients.

Liquid dosage forms for oral administration of the formulations provided herein include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations provided herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention as an active ingredient. A compound of the invention may also be administered as a bolus, electuary, or paste.

In solid dosage forms of the invention for oral administration (e.g., capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol, glycerol monostearate, and non-ionic surfactants; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. Compositions described herein may also be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Pharmaceutical compositions provided herein suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, coconut oils, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

Therapeutic Methods

Provided herein are methods of treating motor neuron disease or disorder in a subject by administering to the subject (e.g., a subject in need thereof) a composition disclosed herein (e.g., a composition comprising a compound of Formula I or Formula II, such as nicotinamide riboside and/or a compound of formula III, such as pterostilbene). In some aspects, provided herein are methods of slowing or reversing the progression of motor neuron degeneration in a subject comprising administering to the subject a composition disclosed herein (e.g., a composition comprising a compound of Formula I or Formula II, such as nicotinamide riboside and/or a compound of Formula III, such as pterostilbene). In some embodiments, motor neuron degeneration refers to the death of neurons and/or the loss of neuron function.

In some embodiments, the subject may have or be predisposed to a motor neuron disease (e.g., amyotrophic lateral sclerosis (ALS), such as medulla ALS or brainstem ALS). A motor neuron disease or disorder may be any disease or disorder that affects the function or structure of motor neuron. As used herein, a motor neuron diseases include progressive diseases that result in loss of function of motor neurons, or nerves, in the brain and spinal cord. Examples of motor neuron diseases include amyotrophic lateral sclerosis (ALS), hereditary spastic paraplegia (HSP), primary lateral sclerosis (PLS), progressive muscular atrophy (PMA), progressive bulbar palsy (PBP), pseudobulbar palsy, or a spinal muscular atrophy. A motor neuron disease may affect the upper motor neurons or the lower motor neurons.

Actual dosage levels and administration regimen of the compositions disclosed herein may be varied so as to obtain an amount of a compound of Formula I or Formula II (e.g., nicotinamide riboside) and/or a compound of Formula III (e.g., pterostilbene) that is effective to achieve the desired therapeutic response for a particular patient, composition, and mode of administration, without being toxic to the patient.

In some embodiments, administration of the composition comprises administration of the composition in one or more dose(s). In some embodiments, administration of the composition comprises administration of the composition in one or more, five or more, ten or more, twenty or more, thirty or more, forty or more, fifty or more, one hundred or more, or one thousand or more dose(s). In some embodiments, the dose comprises at least 100 mg, at least 200 mg, at least 300 mg, at least 400 mg, at least 500 mg, at least 600 mg, at least 700 mg, at least 800 mg, at least 900 mg, at least 1000 mg, at least 1100 mg, at least 1200 mg, at least 1300 mg, at least 1400 mg, at least 1500 mg, at least 1600 mg, at least 1700 mg, at least 1800 mg, at least 1900 mg, at least 2000 mg, at least 2100 mg, at least 2200 mg, at least 2300 mg, at least 2400 mg, at least 2500 mg, at least 2600 mg, at least 2700 mg, at least 2800 mg, at least 2900 mg, or at least 3000 mg, of a compound of Formula I or Formula II (e.g., nicotinamide riboside). In some embodiments, the dose comprises at least 5 mg, at least 10, at least 20 mg, at least 30 mg, at least 40 mg, at least 50 mg, at least 60 mg, at least 80 mg, at least 100 mg, at least 120 mg, at least 140 mg, at least 160 mg, at least 180 mg, at least 200 mg, at least 220 mg, at least 240 mg, at least 260 mg, at least 280 mg, at least 300 mg, at least 320 mg, at least 340 mg, at least 360 mg, at least 380 mg, at least 400 mg, at least 500 mg, at least 600 mg, at least 700 mg, at least 800 mg, at least 900 mg, or at least 1000 mg of a compound of formula III (e.g., pterostilbene).

The compositions disclosed herein may be administered over any period of time effective to achieve the desired therapeutic response for a particular patient, composition, and mode of administration, without being toxic to the patient. The period of time may be at least 1 day, at least 10 days, at least 20 days, at least 30, days, at least 60 days, at least three months, at least six months, at least a year, at least three years, at least five years, or at least ten years. The dose may be administered when needed, sporadically, or at regular intervals. For example, the dose may be administered monthly, weekly, biweekly, triweekly, once a day, or twice a day.

In some embodiments, the subject is given a test to measure the general progression or symptomatic progression of a motor neuron disease. In some embodiments, the subject is given a motor function test and/or a cognition and conduct function test. The motor function test may be Revised Amyotrophic Lateral Sclerosis Functional Rating Scale (ALSFRS-R). The cognition and conduct test may be Complutense Verbal Learning Test (TAVEC), Symbol Digit Modalities Test (SDMT), Verbal Fluency Test, Digit Span (Wechsler Memory Scale III), D2 Attention Test, Wechsler Memory Scale III for Letters and Numbers, London Tower Test, Stroop test, Frontal System Behavior Scale (FrSBe), and/or Brief Test (subjective conduct). In some embodiments, subjects are given both motor function and cognitive function tests. Motor function or cognitive functions tests may be given to the subject once or multiple times.

In some embodiments, the method further comprises measuring a feature (e.g., a feature associated with inflammation) in the subject. In some embodiments, the feature is measured in a blood test. Examples of features that may be tested are the level of a cytokine, level of amyloid A protein, level of macrophage activation marker neopterin, level of creatine phosphokinase (CPK), level of erythrocyte sedimentation rate, level of C-reactive protein, plasma viscosity, and/or white blood cell count. In some embodiments, the cytokine is proinflammatory cytokine. In some embodiments, the cytokine is an anti-inflammatory cytokine. Examples of cytokines include, but are not limited to, TNFα, IFNγ, IL-1, IL-6, IL-8, or TGFβ.

In some embodiments, the method further comprises administering a fatty acid supplement to the subject. In some embodiments, the fatty acid supplement comprises an oil. The oil may be processed (e.g., refined, bleached, or deodorized). In other embodiments, the oil is unprocessed or a virgin oil. In some embodiments, the fatty acid supplement is derived or fractionated from a source to yield separated fatty acids. In some embodiments, the oil is a coconut oil. Coconut oil, as used herein, may include any oil produced by the nut of the coconut palm. Fatty acids found in the supplements disclosed herein may be short-chain fatty acids, medium chain fatty acids, or long chain fatty acids. Exemplary fatty acids that may be found in the supplement include, but are not limited to, caproic acid, caprylic acid, capric acid, lauric acid, myristic acid, palmitic acid, palmitoleic acid, stearic acid, oleic acid, linoleic acid, and/or linolenic acid. The fatty acid supplement disclosed herein may comprise saturated fatty acids, unsaturated fatty acids, monounsaturated fatty acids, and/or polyunsaturated fatty acids. In some embodiments, the fatty acid supplement may comprise a hydrogenated oil. Fatty acid supplements may comprise one or more fatty acid(s). Actual dosage levels and administration regimen of the fatty acid supplement disclosed herein may be varied so as to obtain an amount of fatty acid supplement that is effective to achieve the desired therapeutic response for a particular patient, composition, and mode of administration, without being toxic to the patient.

EXEMPLIFICATION

Example 1: Pilot Study in ALS Patients

ALS patients develop insidious loss of function or gradual, slowly progressive, painless weakness in one or more regions of the body, without changes in the ability to feel, and no other cause is immediately evident. In lower motor neuron (LMN, spinal cord) involvement, fasciculations may occur early on in the disease, particularly in the tongue and limbs. Patients with upper motor neuron (UMN, brain) involvement generally are hyperreflexic and stiff. Reflexes may be diminished due to LMN involvement. UMN symptoms may include spasms and sudden, uncontrolled straightening movements of the lower limbs. As ALS progresses, muscle atrophy becomes more apparent, and spasticity may compromise gait and manual dexterity. Immobility, if coupled with spasticity, may lead to the development of painful joint contractures. Muscle cramps are common. In some patients, persistent stiffness or cramping of muscles may stress the related joints and the back. Some experience increasing difficulty moving, swallowing (dysphagia), and speaking or forming words (dysarthria). Symptoms of UMN involvement include tight and stiff muscles (spasticity) and exaggerated reflexes (hyperreflexia).

The patients involved in the study suffer of ALS at different levels of progression but most show variable/ constant muscle fasciculations, numbness, spasms, stiffness, and/or joint contractures.

Sixty patients with ALS will be split into 5 groups. Group 1 will be control (no treatment), group 2 is administered placebo, group 3 is given a fatty acid supplement (coconut oil), group 4 is given BASIS (nicotinamide riboside and pterostilbene), and group 5 is given Basis in combination with a fatty acid supplement. Patients may be given motor function and cognitive function tests to determine the progression of disease symptoms in the subject Inflammation related parameters, including cytokines (e.g., TNFa, IFNg, IL-1, IL-6, IL-8, or TGFb), amyloid A protein (low molecular weight acute phase protein, which is produced primarily by the liver in response to pro-inflammatory cytokines), macrophage activation marker neopterin, CPK, erythrocyte sedimentation rate, C-reactive protein, plasma viscosity, and white blood cell count may be measured in the patient during the study.

After sixteen days of the study, patients receiving Basis have experienced a decrease of symptomatology related to axon function degeneration. In addition, patients reported being unable to sleep well because of muscle-related symptomatology. However, after BASIS administration, patients report an increase in the ability to sleep.

Example 2: Case Study

A subject diagnosed with ALS showing progressive loss of motor function was administered BASIS for four weeks. Prior to administration, the subject was not able to locomote and subject's muscles were non-responsive to motor function tests. After four weeks of treatment with BASIS, the subject showed improved motor functioning.

Example 3: Nicotinamide Riboside and Pterostilbene Efficacy in Amyotrophic Lateral Sclerosis: a Randomized Placebo-Controlled Pilot Study Objective of this Example To evaluate the efficacy and tolerability of the combination of nicotinamide riboside (a form of vitamin B3) and pterostilbene (a natural polyphenol) (NR+Pter) in patients with amyotrophic lateral sclerosis (ALS).

Methods

This was a single-center, prospective, double-blind, randomized, placebo-controlled pilot study. Patients with ALS were randomized to receive either NR+Pter or placebo, and underwent active evaluation for 4 months.

Results

In total, 27 patients were randomized. As compared to placebo, patients treated with NR+Pter showed a significant improvement on the ratio skeletal muscle/fat weight, the ALS functional rating scale—revised (ALSFRS-R) score, the forced vital capacity (FVC), and the Medical Research Council (MRC) scale for muscle strength.

Classification of Evidence

This study provides Class II evidence that for patients with ALS the association of NR and Pter was significantly better than placebo.

Glossary

ALS=amyotrophic lateral sclerosis; NR=nicotinamide riboside; Pter=pterostilbene; ALSFRS-R=ALS Functional Rating Scale—revised; FVC=forced vital capacity; MRC=Medical Research Council; SARM1=sterile alpha and TIR motif-constraining 1; ULN=upper limit of normal; BIM=body mass index; EMG=electromyogram; mtMP=mitochondrial membrane potential;

mtPTP=mitochondrial permeability transition pore complex; Nrf2=nuclear erythroid-related factor 2; GSH=glutathione.

Methods Study Design Overview and Eligibility

This study was a single-center, randomized, double-blind, placebo-controlled parallel-group pilot trial of NR+Pter-treated versus placebo-treated patients with ALS. The main aim was to assess the efficacy of the combination based on standard clinical criteria. Eligible participants were 18 years of age or older, female (not lactating, negative pregnancy test and agrees to use an effective method of birth control) and male, diagnosed with probable or definite (sporadic or familial) ALS by El Escorial criteria (Brooks 2000), and with an onset of symptomatology for more than 6 months. All patients also received riluzole treatment according with standard dosage. Exclusion criteria were: tracheostomy, invasive ventilation, or non-invasive positive pressure ventilation; gastrostomy; evidence of major psychiatric disorder or clinically evident dementia; diagnosis of a neurodegenerative disease in addition to ALS; have current medication apart from riluzole; have a recent history (within the previous 6 months) or current evidence of alcohol or drug abuse; have concurrent unstable disease involving any system e.g. carcinoma other than basal cell carcinoma, any cardiac dysrhythmia, myocardial infarction, clinical or ECG signs of myocardial ischemia, cardiac insufficiency, angina symptoms, current symptoms of coronary artery disease; having a baseline QTc (Bazett)>450 msec for males and >470 msec for females; patients with known hepatitis B/C or HIV positive serology; have renal impairment defined as blood creatinine>2×ULN (upper limit of normal); have hepatic impairment and/or liver enzymes (ALAT or ASAT)>3× ULN; hemostasis disorders or current treatment with oral anticoagulants; participated in any other investigational drug or therapy study with a non-approved medication, within the previous 3 months; patients without medical insurance.

Sample Size, Randomization, and Blinding

Patients were randomly assigned. The number of patients evaluated per group were: placebo (n=14 at baseline and 2 months, 10 at 4 months), NR+Pter (n=13 at baseline and 2 months, 10 at 4 months). The study was double blinded, including patients and the health staff, except for the directors (J.E.R., J.M.E.).

Diet

All patients were fed a Mediterranean style diet (approx. 2,300 Kcal/day) (see e.g. Davis 2015). Patients in the placebo group received capsules containing brown sugar. The combination of NR+Pter was administered at a dose of approx. 15 mg of NR and 2.5 mg of t-Pter/Kg×day. The diet in the placebo and the NR+Pter group was 55% carbohydrates+30% fat+15% proteins. Carbohydrates in the diet corresponded to slow-release carbohydrate foods. Vitamins and oligoelements in the diet of both groups were adjusted following recommended dietary allowance by the EFSA (European Food Safety Authority).

Follow-Up, Outcomes, and Data Collection

Follow-up visits were scheduled at baseline (time 0), 2 and 4 months of treatment. Neurologic examination was performed at the 3 time points and the following items recorded: anthropometric analysis, ALSFRS-R total score, FVC, strength of the muscles as graded by MRC grading scale, electromyography to evaluate the electrical activity produced by skeletal muscles. During the whole duration of the study, the patients had permanent communication with the medical team and their evolution was informed weekly.

Anthropometry

Fat and skeletal muscle weights were calculated following standard anthropometric procedures (Wang 2000). Fat and skeletal muscle weight data refer to the change observed comparing 2 or 4 months versus baseline.

ALSFRS-R Score

This validated rating instrument for monitoring the progression of disability in patients with ALS (Kollewe 2008) is based on 12 items, each of which is rated on a 0-4 point scale. The rate of total functional disability thus ranges from 0 (maximum disability) to 48 (normal) points.

FVC

This clinically meaningful predictor of survival and disease progression in ALS patients (Czaplinski 2006) was measured using a Datospir touch spirometer from Sibelmed (Barcelona, Spain), and expressed as the % of the standard value that corresponds to human adults depending on sex, weight and age parameters) (Garcia-Rio 2013).

MRC Scale

The muscle strength was evaluated based on an 11-steps modified MRC grading scale (www.medscape.com) (5, normal power; 5−, equivocal, barely detectable weakness; 4+, definitive but slight weakness; 4, able to move the joint against combination of gravity and some resistance; 4—, capable of minimal resistance; 3+, capable of transient resistance but collapses abruptly; 3, active movement against gravity; 3−, able to move against gravity but not through full range; 2, able to move with gravity eliminated; 1, trace contraction; 0, no contraction). MRC scoring was obtained in each patient for 8 different muscles [right (R) and left (L) biceps, triceps, quadriceps and tibial]. To calculate the total MRC index a progressively increasing number from 0 (0 in the scale) to 10 (5 in the scale) was given to each step and each muscle. The total MRC index per patient corresponds to the sum of the numbers given to all the 8 muscles.

Electromyography

A surface electromyogram (EMG) measuring device (BTS FreeEMG 300, BTS S.p.A., Milan, Italy) was used to measure muscle activity in the same muscles indicated above for the MRC index. EMG signals per muscle were analyzed by the root mean square (RMS) method, which reflects the physiological activity in the motor unit during contraction. The RMS represents the square root of the average power of the EMG signal for a given period of time (e.g. Boe 2008).

Statistical Methods

Data are presented as mean values±SD for the number of different experiments. Statistical analyses were performed using Student's t-test. *P<0.05, and **P<0.01 comparing 2 or 4 months versus baseline in all groups; +P<0.05, and ++P<0.01 comparing NR+Pter versus placebo.

Results

Thirty-two ALS patients fulfilling inclusion criteria were randomly distributed in two groups of 17 (placebo) and 15 (NR+Pter) patients. The study began by the end of February 2017. Along the study some patients withdrew due to different causes. During the initial period between 0 and 2 months, 3 patients of the placebo group (1 case due to urinary infection, 1 case of pneumonia, and 1 death caused by respiratory paralysis) and 2 patients of the NR+Pter group (1 case due to gastroenteritits, 1 death caused by pneumonia) were eliminated. During the period between 2 and 4 months, 4 more patients of the placebo NR+Pter group (1 traumatology-related event, 1 hepatitis, and 1 profound mental depression) were also separated. As shown in Table 1, where demographic and clinical features of the patients are displayed, mean age in both groups was of 55-56 years. Body weight and BIM (body mass index) values were not significantly different when patients of both groups and treatments were compared along the study. However, NR+Pter treatment induced a significant change in fat (decrease) and skeletal muscle (increase) weights (Table 1). These changes associated with a significant increase in the ALSFRS-R score and FVC performance of the NR+Pter group at 4 months (as compared to baseline) (Table 1). These improvements also associated with muscle strength and activity data. As shown in Table 2, the total MRC scale index increased in the NR+Pter-treated group comparing baseline and 4 months, and comparing NR+Pter versus placebo values; whereas the same index decreased in placebo-treated patients during the same period of time. Changes in EMG values were only found significant for 1 muscle (triceps) at 4 months comparing NR+Pter versus placebo (Table 2).

TABLE 1

Demographic characteristics and clinical features for randomized ALS patients at baseline (BL) and after 2-4 months (2 M-4 M) of treatment.

|  |  | Placebo | BASIS | BASIS + Coconut Oil |
|---|---|---|---|---|
| Age (years) | BL | 55.6 ± 10.5 | 56.7 ± 9.4 | 53.8 ± 7.0 |
| Male/Female | BL | 8/6 | 9/4 | 5/2 |
|  | 4 M | 6/4 | 8/2 | 5/2 |
| Family History of ALS (No. of cases) |  | 0 | 1 | 0 |
| Onset Bulbar/Spinal | BL | 4/10 | 3/10 | 5/2 |
|  | 4 M | 1/9 | 1/9 | 5/2 |
| Deaths |  | 1 (ALS) | 1 (pneumonia) | 1 (accident) |
| Body Weight (kg) | BL | 70.2 ± 8.4 | 69.4 ± 7.9 | 68.6 ± 9.9 |
|  | 2 M | 68.8 ± 7.9 | 68.4 ± 7.7 | 68.9 ± 8.6 |
|  | 4 M | 64.5 ± 8.4 | 69.3 ± 9.3 | 68.6 ± 8.1 |
| BIM (kg/m$^3$) | BL | 24.6 ± 2.1 | 24.7 ± 3.7 | 25.0 ± 4.8 |
|  | 2 M | 23.8 ± 1.9 | 23.5 ± 2.3 | 25.1 ± 3.7 |
|  | 4 M | 22.3 ± 2.4 | 24.0 ± 2.0 | 24.8 ± 2.6 |
| Fat Weight (kg) | 2 M-BL | 0.92 ± 0.57 | −1.18 ± 0.35++ | −0.73 ± 0.44++ |
|  | 4 M-BL | 1.15 ± 0.41 | −1.61 ± 0.44++ | −1.17 ± 0.26++ |
| Skeletal Muscle Weight (kg) | 2 M-BL | −0.58 ± 0.31 | 0.41 ± 0.27++ | 0.72 ± 0.40++ |
|  | 4 M-BL | −1.14 ± 0.47 | 0.41 ± 0.16++ | 0.95 ± 0.33++ |
| ALSFRS-R Score (0-48) | BL | 41.5 ± 5.2 | 38.8 ± 4.9 | 40.7 ± 5.4 |
|  | 2 M | 38.5 ± 6.0 | 42.4 ± 4.7 | 41.5 ± 5.0 |
|  | 4 M | 35.2 ± 3.1 | 41.3 ± 2.8+ | 40.8 ± 4.2 |
| FVC (%) | BL | 92.3 ± 12.6 | 95.3 ± 7.4 | 89.1 ± 10.5 |
|  | 2 M | 88.5 ± 9.7 | 101.4 ± 4.5(n = 11) | 105.0 ± 5.5*++ |
|  | 4 M | 77.8 ± 10.0 | 97.2 ± 7.4++ | 101.4 ± 4.6++ |
| Duration of Symptoms (Months up to Baseline) |  | 24.0 ± 9.6 | 20.6 ± 12.5 (n = 11; 1 case = 64) | 16.4 ± 7.0 (n = 6; 1 case = 72) |

TABLE 2

Treatment-induced changes in muscle strength in ALS patients.

|  |  | Placebo |  |  | BASIS |  |  | BASIS + coconut oil |  |  |
|---|---|---|---|---|---|---|---|---|---|---|
| Total MRC Scale Index | BL | 46 ± 3 |  |  | 41 ± 3 |  |  | 44 ± 4 |  |  |
|  | 2 M | 36 ± 4** |  |  | 50 ± 3**++ |  |  | 55 ± 5*++ |  |  |
|  | 4 M | 34 ± 7** |  |  | 57 ± 15**+ |  |  | 58 ± 10**++ |  |  |
| EMG |  | BL | 2 M | 4 M | BL | 2 M | 4 M | BL | 2 M | 4 M |
| Biceps | R | 233 ± 87 | 201 ± 56 | 185 ± 46 | 285 ± 103 | 292 ± 87 | 273 ± 77 | 190 ± 54 | 202 ± 79 | 174 ± 76 |
|  | L | 245 ± 91 | 246 ± 101 | 190 ± 38 | 264 ± 86 | 261 ± 97 | 276 ± 84 | 211 ± 46 | 239 ± 114 | 174 ± 55 |
| Triceps | R | 187 ± 53 | 134 ± 71 | 126 ± 51 | 170 ± 66 | 194 ± 74 | 212 ± 55+ | 165 ± 58 | 183 ± 65 | 192 ± 59 |
|  | L | 211 ± 77 | 177 ± 65 | 155 ± 44 | 234 ± 59 | 250 ± 71 | 327 ± 74+ | 190 ± 45 | 207 ± 58 | 201 ± 74 |
| Quadriceps | R | 151 ± 46 | 136 ± 44 | 141 ± 35 | 133 ± 36 | 147 ± 75 | 152 ± 50 | 179 ± 64 | 190 ± 78 | 190 ± 53 |
|  | L | 177 ± 65 | 146 ± 68 | 133 ± 47 | 138 ± 55 | 148 ± 69 | 148 ± 39 | 190 ± 88 | 184 ± 77 | 176 ± 46 |

TABLE 2-continued

Treatment-induced changes in muscle strength in ALS patients.

| Tibial | R | 167 ± 49 | 135 ± 53 | 125 ± 42 | 101 ± 57 | 97 ± 50 | 164 ± 44 | 248 ± 102 | 240 ± 68+ | 274 ± 89+ |
|--------|---|----------|----------|----------|----------|---------|----------|-----------|-----------|-----------|
|        | L | 139 ± 50 | 116 ± 55 | 94 ± 33  | 122 ± 57 | 123 ± 68| 182 ± 56 | 208 ± 90  | 240 ± 71+ | 197 ± 71+ |

Data are presented as mean values±SD for the number of different experiments. Statistical analyses were performed using Student's t-test. *P<0.05, and **P<0.01 comparing 2M versus BL in all groups; +P<0.05, and ++P<0.01 comparing BASIS or BASIS+coconut oil versus Placebo.

CONCLUSIONS

1. Patients administered BASIS, as compared to placebo-treatment, experienced a significant decrease in fat weight and an increase in skeletal muscle weight.
2. Patients administered BASIS, as compared to placebo-treatment, experienced an increase the ALSFRS-R score and vital capacity.
3. Patients administered BASIS, as compared to Placebo-treatment, experienced significant increases the MRC scale index. When comparing the EMG of 4M vs BL, patients administered BASIS maintained or increased muscle activity, whereas patients administered placebo controls showed decreased muscle activity.

Example 4: Assessment of Motor Coordination and Balance in Rodent Models of Amyotrophic Lateral Sclerosis Methods: Mice Wild-type and transgenic FUS $R_{521}C$. Strain Name: B6;SJL-Tg(Prnp-FUS*$R_{521}$C)3313Ejh/J. Genetic Background: Transgene injected into B6SJL oocytes. Maintained on $C_{57}BL/6$, therefore subsequent generations have a higher percentage of $C_{57}BL/6$. The Jackson Lab: Stock #026406. At a young age, this transgenic mouse develops severe motor impairment and other ALS-related phenotypes. Notably, it develops robust neuronal loss in the spinal cord, denervation of neuromuscular junctions, and muscle atrophy. Phenotype development is swift—detectable within weeks of birth—and the mice decline rapidly. Most mice in the original N1F1 generation reached end-stage within three months (Qiu et al. 2014). At one month of age, the mice express mutant FUS at levels approximately equal to endogenous FUS levels in the brain and spinal cord. The majority of the transgenic FUS-$R_{521}$C protein in these mice is nuclear. Cytoplasmic protein is occasionally detected; however, less than 10% of spinal motor neurons contain cytoplasmic FUS inclusions. Endogenous FUS protein, but not transgenic protein, appears in dendrites as a punctate pattern. Similar to endogenous FUS, FUS-$R_{521}$C protein is detected in astrocytes and oligodendrocytes, but not in microglia.

The mice develop prominent neuronal loss in the spinal cord. At birth, the number of spinal motor neurons is normal. However, by day 16, the number of ChAT-positive neurons in the anterior horn of the spinal cord is reduced by 20 percent. Degeneration continues, and by end stage, only about half of the neurons remain. The surviving motor neurons have reduced dendritic complexity, synaptic defects, and DNA damage. There is no detectable loss of cortical neurons; however, neurons in the sensorimotor cortex have reduced dendritic complexity and reduced synaptic density.

Despite modest transgene expression, FUS-$R_{521}$C mice exhibit a variety of motor impairments from a young age, including spastic paraplegia and abnormal hindlimb clasping when lifted by the tail. They also have gait abnormalities, including reduced distance between their hind paws during walking. Performance on the Rotarod is poor.

The majority of mice in the original N1F1 generation reached end stage by postnatal day 100. Mice in subsequent generations (e.g., N2F2, N2F3), which have greater $C_{57}BL/6$ contribution, live longer; about 40 percent reached end stage by postnatal day 200. Both male and female mice show similar disease phenotypes. Hemizygous males may be sterile, or at least have a much reduced breeding capacity (Eric Huang, personal communication, March 2016).

Specific Phenotype Characterization

Cortical Neuron Loss. No detectable loss of cortical neurons; however, neurons in the sensorimotor cortex show reduced dendritic complexity and reduced synaptic density.

Lower Motor Neuron Loss. No detectable difference in spinal motor neurons at $P_0$. At P16, about 20% loss of ChAT-positive neurons in the anterior horn of cervical spinal cord. At P30-P60, about 50% loss of anterior horn neurons. Remaining motor neurons show reduced dendritic complexity and synaptic density.

Gliosis

Prominent increase in microgliosis and astrogliosis in the anterior horn of the spinal cord by end stage.

Muscle Atrophy

The majority of mice have severe skeletal muscle atrophy in the hindlimb by end stage.

Motor Impairment

Early postnatal motor impairment, including abnormal hindlimb clasping when lifted by the tail, gait abnormalities, and impaired Rotarod performance.

Body Weight

Early postnatal growth is retarded, and the mice experience progressive loss of body weight.

Premature Death

The majority of mice in the N1F1 generation reached end stage and were sacrificed by postnatal day 100. Mice in subsequent generations live longer: about 40% reach end stage by postnatal day 200.

Treatment

Nicotinamide riboside and pterostilbene will be administered orally: 185 mg of nicotinamide riboside and 30 mg of pterostilbene/Kg×day

Neurological Score

Neurological score has been performed in mice weekly starting at postnatal day 20 (P20) by visual inspection. Neurological score will be based on the scale of Weydt et al. (2003). The scores from "0" to "5" are defined as follow: "0" indicates a healthy mouse with no classical signs of ALS; "1" indicates the presence of tremors in the hind legs that occur in early disease stage; "2" indicates that mice have difficulty in separating their hind legs when suspended by their tails, which is indicative of muscle weakness; "3" is given when mice exhibit difficulty walking, either stumbling or wobbling; "4" is given when mice were unable to walk on all four legs and drag their hind legs; "5" is given when mice were unable to right themselves after 30 seconds. When the animals reach a score of "4", the access to food and water will be facilitated by placing food pellets on the cage floor to all transgenic mice. Reaching a score of "5", the animals will be euthanized for ethical reasons. Onset is defined as the earliest time when the mice show symptoms (score <4) for ≥2 consecutive weeks.

Rotarod, Hanging Wire and Inclined Plane

Beginning at P20, motor function using a rotarod apparatus will be analyzed (Touchscreen Rota Rod, Panlab). Each animal will be given three trials and the maximum period (seconds) that it could remain on a rotating axle (3.5 cm diameter; speed of rotation:

15 rpm) without falling will be measured. The test will bestopped after an arbitrary limit of 180 seconds. In the first 2 weeks, an adaptation period of three trials will be performed before the beginning of the recordings.

Hanging wire test will begin at P20 and will be performed weekly, 24 hours before the rotarod test. Animals will be placed on the wire lid of a conventional housing cage. The lid will be gently turned upside down, 50 cm above a soft surface to avoid injuries. The latency to fall will be timed. Each mouse will be given up to three attempts for a maximum of 180 seconds and the longest period will be recorded.

The inclined plane apparatus consists of a hinged wooden board which will be set at an angle of 0°. The animals at P20 will be placed head up on the board and it will be raised at constant speed until the mouse slip out the board. The maximum angle reached without slip out will be recorded.

Tail Elevation

Tail elevation will be determined weekly starting at P20 by visual inspection using the tail score during the assessment of neurological score. Tail score will based on the SHIRPA tail scale, procedure developed by Rogers et al. in MRC, United Kingdom (Niimi and Takahashi 2009; Rogers et al. 1997). The scores "0" to "3" are defined as follows: "0" indicates vertical position of the tail (maximum elevation); "1" indicates horizontally extended tail; "2" indicates dragging tail for more than 20 seconds; "3" will be given when the tail displayed proximal contracture and distal laxity (mice with this score will be in the terminal phase of the disease).

Automatic Evaluation by Infrared Motion Sensor Activity System

The motor behavior will be evaluated in an open-field by automatic recording of motor activity based on movement time, without any intervention by the investigator, using an infrared motion sensor monitor (Coulbourn Instruments, USA) as described previously (Andrade et al. 2010). The experimental room will be diffusely illuminated and kept at constant temperature and humidity. Mice will be individually placed in polyetilene cages (37×17×30 cm), which have an infrared motion sensor on the top of the wall, and the register will be done in blocks of 2-minutes observation time during 30 minutes. From the resulting data, the following dependent measures parameters will be calculated: without-movement time, which is defined as the mean of the time (seconds) during which the animal did not move or moved for a time less than 0.01 second during the observation time; without-movement events are the mean number of events registered at every without-movement time during the observation time; small-movement time, which is defined as the mean of the time (seconds), during which the animal moved between a time interval superior to 0.01 second but inferior to 0.1 second, during the observation time; small movement events are the mean number of events registered at every small-movement time, during the observation time; large-movement time, which is defined as the mean of the time (seconds) during which the animal moved in a time interval superior to 1.0 second; large-movement events are the mean number of events registered at every large-movement time, during the observation time. The data will be transferred to a computer and analyzed by specific software. Only the numbers of without-movement, small-movement and large movement events will be used for evaluation. The graphics will be plotted per periods corresponding to: first period (P40-60), second period (P70-80), third period (P90-100) and fourth period or end stage of disease (P110-120).

Latency, velocity and amplitude in the conduction of the nerve input in the sciatic nerve (Alves et al. 2011). The electrophysiological measurements will be recorded at P20, P40, P60, P80, P100 and P120 in mice anesthetized with ketamine chlorhydrate (Ketalar) and diazepam (Valium) (1 ml/kg of a solution containing 11.25 mg ketalar and 0.375 mg of valium; IP).

Normal body temperature will be preserved using a heater. The sciatic nerve will be exposed and the animals submitted to electrophysiological evaluation consisting of measurement of compound motor action potential (CMAP). Such evaluation aims at checking nerve electrophysiological integrity and measuring parameters used in calculating the mean between the amplitudes, the mean between the latencies and the mean between the conduction velocities of each potential. To reduce possible interference, 2 ground electrodes will be installed after surgical nerve exposure, one of which is a monopolar straight needle electrode (26 G) placed within the muscle adjacent to the nerve; the other ground electrode will be manufactured from 316 L stainless steel wire and its extremity will be of helical configuration so as to surround the nerve and increase the contact area. The bipolar electrodes for CMAP stimulation will be manufactured from 316 L stainless steel wire 0.5 mm in diameter, with anode—cathode separatio n of 1 mm. Recordings will be made on a 2-channel electromyography system (Keypoint portable; Medtronic, Skovlunde, Denmark), with the high-frequency filter set at 5 kHz and the low-frequency filter set at 2 Hz. Electric stimulation produces artifacts; to reduce them, rectangular monophase electric pulses with a pulse width of 0.04 ms will be used. For CMAP measurements the stimulation electrode will be placed on the nerve at distance of 1 cm from the recording electrode placed on the gastrocnemius muscle through percutaneous puncture in the distal third of the paw, ipsilaterally to the surgical procedure, with a coaxial needle. An initial negative deflection and biphasic waveform indicates recording at the motor point. The latency of evoked potentials will be measured in milliseconds. From such recorded potential, the conduction velocity will be calculated using the distance of 1 cm divided by latency.

Pathology

Methodology for isolation, preparation and analysis of the CNS will follow the procedures described in detail by Jordan W H, Young J K, Hyten M J, Hall D G. *Preparation and analysis of the central nervous system.* Toxicol Pathol. 2011 January; 39(1):58-65, hereby incorporated by reference in its entirety.

Example 5: Assessment of the Effect of Nicotinamide Riboside and Pterostilbene on Motor Coordination and Balance in Rodent Models of Amyotrophic Lateral Sclerosis Objective of This Example To evaluate the effect of the association of nicotinamide riboside and pterostilbene on the improvement of motor functions in mouse models of ALS, particularly in comparison to the effect of nicotinamide riboside and resveratrol.

Methods

Mice

1. B6.Cg-Tg(SOD1*G93A)1Gur/J (https://www.jax.org/strain/004435)

Mice hemizygous for this SOD1-G93A (also called G93A-SOD1) transgene were viable and fertile, with transgenic expression of a G93A mutant form of human SOD1. This founder line (often referred to as G1H) was reported to have high transgene copy number. Hemizygotes exhibited a phenotype similar to amyotrophic lateral sclerosis (ALS) in humans; becoming paralyzed in one or more limbs with paralysis due to loss of motor neurons from the spinal cord. Motor neuron degeneration has been associated with function and/or degeneration of astrocytes, the major glial cell type of the nervous system. Transgenic mice had an abbreviated life span: 50% survive at 157.1+/−9.3 days (in contrast to the mixed B6SJL background where 50% survival was observed at 128.9+/−9.1 days). Female hemizygotes were poor breeders, and rarely produced more than one litter before the onset of disease. In contrast to LPS-induced microglia and activated M1/M2 macrophages, spinal cord microglia activated by disease progression did not upregulate genes that display a bias to either an M1 (neurotoxic) phenotype or an M2 (protective) phenotype. The pattern of gene expression in SOD1G93A activated microglia represented a unique ALS-specific signature. These SOD1-G93A (also called G93A-SOD1) transgenic mice were useful in studying neuromuscular disorders, including Amyotrophic Lateral Sclerosis.

The SOD1-G93A transgene was designed with a mutant human SOD1 gene (harboring a single amino acid substitution of glycine to alanine at codon 93) driven by its endogenous human SOD1 promoter. This transgene was injected into fertilized B6SJLF1 mouse eggs and founder animals were obtained. Transgenic mice on a mixed B6SJL genetic background were sent to The Jackson Laboratory (as Stock No. 002726). Upon arrival, some mice were backcrossed to C57BL/6J for at least 10 generations to generate this congenic strain (Stock No. 004435).

2. Control/Noncarrier

B6SJLF1/J (https://www.jax.org/strain/100012) mice were produced by a cross between C57BL/6J (B6) female mice with SJL/J (SJL) male mice. B6SJLF1/J mice were heterozygous for B6 and SJL alleles at all loci in their genome. This strain was often used in the production of transgenic mice.

Neuropathology

Although the SOD1 G93A transgene was expressed widely, pathology in this model was largely restricted to the spinal cord (especially the lumbar cord), brainstem, descending spinal tracts, and neuromuscular junctions. A variety of pathological hallmarks developed in the spinal cord prior to the onset of clinical symptoms, including mitochondrial vacuolization (Dal Canto and Gurney, *Brain Res.* 1995; 676(1):25-40), Golgi fragmentation (Mourelatos et al., *Proc Natl Acad Sci USA.* 1996; 93(11):5472-7), neurofilament-positive inclusions (Tu et al., *Proc Natl Acad Sci USA.* 1996; 93(7):3155-60), Lewy body-like inclusions (Dal Canto and Gurney, *Brain Res.* 1995; 676(1):25-40), and cytoplasmic SOD1 aggregates (Johnston et al., *Proc Natl Acad Sci USA* 2000; 97(23):12571-6). Neuromuscular junctions degenerated around 47 days of age; fast-fatiguable motor neurons were affected first (Frey et al., *J Cell Biol.* 2000; 149(7):1443-54; Pun et al., *Nat Neurosci.* 2006; 9(3):408-19). Spinal motor neurons then died off, with about a 50 percent reduction in the cervical and lumbar segments by end-stage (Chiu et al., *Mol Cell Neurosci.* 1995; 6(4): 349-62).

Neuropathology was not restricted to lower motor neurons. In upper motor neurons, signs of degeneration included swollen neurites, Gallyas silver-positive aggregates, vacuoles, and neuritic spheroids. These changes occurred at about five months of age, after degeneration in the spinal cord was underway, and generally did not progress to outright neuronal loss (Leichsenring et al., *Brain Res.* 2006; 1096(1):180-95). Degeneration of cranial nuclei, such as the trigeminal, facial, and hypoglossal nerves, has been observed (Angenstein et al., *Neuroreport.* 2004; 15(14): 2271-4; Zang et al., *Eur J Neurosci.* 2004; 20(7):1745-51) and there was age-dependent regression of descending corticospinal, bulbospinal, and rubrospinal tracts (Zang and Cheema, *Neurosci Lett.* 2002; 332(2):99-102).

Gliosis, including the proliferation of reactive microglia and astrocytes, developed in parallel with motor neuron degeneration in the spinal cord. GFAP and MAC1 immunoreactivity indicated an increase in reactive glia by 117 days of age (Hall et al., *Glia.* 1998; 23(3):249-56).

Usage

These mice have been studied extensively over many years, and this research laid the groundwork for updated guidelines about preclinical research in ALS (Ludolph et al., *Amyotroph Lateral Scler.* 2010; 11(1-2):38-45). Recommendations for experimental design included using enough mice to sufficiently power experiments, using experimental cohorts balanced for gender and littermates, and reporting this information in all manuscripts. Given the importance of copy number, quantitative genotyping should be used to ensure that all experimental animals have the expected copy number (Alexander et al., *Brain Res Mol Brain Res.* 2004; 130(1-2):7-15).

Modification Details

These transgenic mice expressed multiple copies of human SOD1 bearing the missense mutation G93A randomly integrated into chromosome 12 of the mice.

Phenotype Summary

Cortical neuron loss: evidence of degeneration (e.g., swollen neurites, Gallyas-positive aggregates, vacuoles, and neuritic spheroids) has been shown in motor cortex. Outright upper motor neuron loss was rare.

Lower motor neuron loss: up to 50% loss of motor neurons in the cervical and lumbar segments of the spinal cord at end-stage was observed.

Cytoplasmic inclusions: inclusion accumulated in the spinal motor neurons from 82 days of age. The inclusions took the form of spheroids or Lewy-body-like inclusions and commonly included a variety of neuronal intermediate filament proteins. TDP-43 positive inclusions were rare.

Gliosis: gliosis developed in parallel with motor neuron degeneration in the spinal cord.

Neuromuscular junction abnormalities: NM junctions degenerated around 47 days of age. Fast-fatigable motor neurons were affected first.

Muscle atrophy: longitudinal MRI has shown reduced muscle volume from 8 weeks of age. Atrophy was progressive. Skeletal muscle, including limb and diaphragm, was affected.

Motor impairment: signs of motor impairment began at 3 months with a shaking tremor that led to paralysis.

Body weight: abnormal body weight was one of the first signs of illness; slowing of growth and a plateauing of weight were observed.

Premature death: mice reached end-stage by 5 months of age. Females typically survived longer (4-7 days longer).

Treatment

Nicotinamide riboside, pterostilbene, and resveratrol were administered orally: 185 mg of nicotinamide riboside and/or 30 mg of pterostilbene or resveratrol per Kg per day were administered to the mice.

Results

Survival Time

Kaplan-Meier curve comparing survival time between groups of mice were shown in FIG. 1. The number of survival mice of different treatment groups at each week was shown in FIG. 2.

Neurological Score

This score was based on the scale of Weydt et al. (Neuroreport 14: 1051-1054, 2003). The scores from "0" to "5" were defined as follow: "0" indicated a healthy mouse with no classical signs of ALS; "1" indicated the presence of tremors in the hind legs that occured in early disease stage; "2" indicated that mice had difficulty in separating their hind legs when suspended by their tails, which was indicative of muscle weakness; "3" was given when mice exhibited difficulty walking, either stumbling or wobbling; "4" was given when mice were unable to walk on all four legs and drag their hind legs; "5" was given when mice were unable to right themselves after 30 seconds. When the animals reached a score of "4", the access to food and water was facilitated by placing food pellets on the cage floor to all transgenic mice. Reaching a score of "5", the animals were euthanized for ethical reasons. Onset was defined as the earliest time when the mice showed symptoms (score <4). Changes over time in the different groups were monitored weekly from week 8 (P50) to week 20 (P140). The number of animals tested per week was identical to that displayed in FIG. 1 for each group. The neurological scores of different groups were shown in FIG. 3.

Tail Elevation Score

This score was based on the SHIRPA tail scale, procedure developed by Rogers et al. (Mamm. Genome 8: 711-713, 1997) in the MRC, United Kingdom. The scores "0" to "3" were defined as follows: "0" indicated vertical position of the tail (maximum elevation); "1" indicated horizontally extended tail; "2" indicated dragging tail for more than 20 seconds; "3" was given when the tail displayed proximal contracture and distal laxity (mice with this score were in the terminal phase of the disease). Changes over time in the different groups were monitored weekly. The number of animals tested per week was identical to that displayed in FIG. 1 for each group. The tail elevation scores of different groups were shown in FIG. 4.

Rotarod Test

Functions of the test included evaluating balance, grip strength and motor coordination of the subjects; especially in testing the effect of experimental drugs. For this test (Rota Rod, Harvard Apparatus, Holliston, Mass.), each animal was given three trials and the maximum period (seconds) that it could remain on a rotating axle (3.5 cm diameter; speed of rotation: 15 rpm) without falling was measured. Each mouse was given up to three attempts for an arbitrary limit of 1200 seconds and the longest period was recorded. Changes over time in the different groups were monitored weekly. The number of animals tested per week was identical to that displayed in FIG. 1 for each group. The rotarod test results for different groups were shown in FIG. 5.

Hanging Wire Test

Motor function and deficit in rodent models of CNS disorders were evaluated. For this test, animals were placed on the wire lid of a conventional housing cage. The lid was gently turned upside down, 50 cm above a soft surface to avoid injuries. The latency to fall was timed. Each mouse was given up to three attempts for a maximum of 180 seconds and the longest period was recorded. Changes over time in the different groups were monitored weekly. The number of animals tested per week was identical to that displayed in FIG. 1 for each group. The hanging wire test results for different groups were shown in FIG. 6.

Inclined Plane Test

For this locomotor rating test, a flat rolling band (Treadmill, Harvard Apparatus) was used and set at an angle of 5°. The animals were placed head up on the board at a constant speed (15 cm/s). The system incorporated a shock grid at the back of the treadmill to deliver a mild electric shock (0.2 mA for a maximum of 3 seconds) if the mouse fell off the board. Each mouse was given two trials and the maximum distance run and the number of electrical stimuli received during the test (not exceeding 3 seconds) were recorded. The test was stopped after an arbitrary limit of 600 seconds or if the animal received an electrical stimuli >3 seconds. Changes over time in performance in the different groups were monitored weekly. Performance was expressed as a ratio between the distance run (m) and the number of electrical stimuli received (not exceeding 3 seconds). Changes over time in the different groups were monitored weekly. The number of animals tested per week was identical to that displayed in FIG. 1 for each group. The inclined plane test results for different groups were shown in FIG. 7.

Motor Activity by Automatic Evaluation

Changes over time in spontaneous activity (locomotion) were measured by means of an Infrared Motion Sensor Activity Monitor (IR Actimeter, Harvard Apparatus) in the different groups indicated in FIG. 1. The IR Actimeter was composed by a two-dimensional (X and Y axes) square frame, a frame support and a control unit. Each frame was composed of 16×16 infrared beams for optimal subject detection. Activity was expressed as the time (in seconds) moving slow (MS, time during which the subject speed is between the resting and the fast thresholds, 2-5 cm/s) or moving fast (MF, time during which the speed of the subject is above the fast threshold, >5 cm/s). Resting period was considered the time period during which the speed of the subject was below the resting threshold (<2 cm/s). The register was performed in blocks of 2-min during the observation time period (30 min). Changes over time in the different groups were monitored weekly. Data were pooled into 4 different periods (weeks 8-11, 12-15, 16-18, 19-20), and shown in FIG. 8. The mean values were calculated using the largest number of slow and fast movements performed by each mouse during the indicated period. The number of animals tested per week was identical to that displayed in FIG. 1 for each group.

Electrophysiological Measurements

Changes over time in evoked Compound Motor Action Potential (CMAP) in the gastrocnemius muscle after stimulation of the sciatic nerve were monitored at P50 (week 8) and P126 (week 18). Recordings were made on a 2-channel electromyography system (Keypoint portable; Medtronic, Skovlunde, Denmark), with the high-frequency filter set at 5 kHz and the low-frequency filter set at 2 Hz. Electric stimulation produces artifacts; to reduce them, rectangular monophase electric pulses with a pulse width of 0.04 ms were used. For CMAP measurements the stimulation electrode was placed on the nerve at distance of 1 cm from the recording electrode placed on the gastrocnemius muscle through percutaneous puncture in the distal third of the paw, ipsilaterally to the surgical procedure, with a coaxial needle. The electrophysiological measurements were shown in FIG. 9. The data of CMAP amplitude were expressed in millivolts, the data of latency were expressed in milliseconds and the data of nerve conduction velocity were expressed in meters per second (m/s). The number of animals tested per time point and group was of n=4.

Pathology

Methodology for isolation, preparation and analysis of the CNS followed the procedures described in detail by Jordan W H, Young J K, Hyten M J, Hall D G. *Preparation and analysis of the central nervous system*. Toxicol Pathol. (2011) January; 39(1):58-65, hereby incorporated by reference in its entirety.

Statistics

Data were presented as mean values±SD for the number of different experiments. Statistical analyses were performed using Student's t-test.

*$P<0.05$ and **$P<0.01$ comparing all SOD1 groups versus WT.

+$P<0.05$ and ++$P<0.01$ comparing all SOD1 groups treated with NR, PT, R or their combinations versus SOD1 untreated controls.

$^a P<0.05$ and $^{aa}P<0.01$ comparing SOD1+NR+PT groups versus SOD1+NR.

Comparisons between SOD1 and SOD1+R groups, or between SOD1+NR and SOD1+NR+R groups, did not show significant differences.

CONCLUSIONS

1. EH301 (NR+PT) increased SOD1 mice survival (FIG. 1, and FIG. 2). The effect of the combination was better than NR (FIG. 1, and FIG. 2). PT alone did not improve survival (FIG. 1, and FIG. 2).
2. Despite the cellular and biochemical evidences of an early motor system dysfunction, the conventional behavioral tests did not detect early motor impairments in SOD1 mouse model. Changes in motor behavior and performance of ALS mice were evaluated using the following standard tests: neurological score (FIG. 3), tail elevation (FIG. 4), rotarod (FIG. 5), hanging wire (FIG. 6), inclined plane/treadmill (FIG. 7), automatic recording of motor activities by means of an infrared motion sensor activity system (FIG. 8), and electrophysiological measurements (amplitude, latency and nerve conduction velocity associated to the motor action potential in the gastrocnemius muscle after stimulation of the sciatic nerve; FIG. 9). The conclusion was that both NR and EH301 (NR+PT) but not PT alone improved motor functions (FIG. 3-FIG. 9). In this regard, EH301 (NR+PT) was superior to NR alone (see FIG. 3, FIG. 5, FIG. 6, FIG. 7, and FIG. 8). But the benefits were only observed in the last weeks of the experiment. Therefore, despite potential biochemical and molecular evidences of an early motor system dysfunction, alterations in motor performance and coordination developed later in time. This fact indicated that activation of physiological adaptations preserved the motor neuron-dependent function. In practice what was evident was a progressive decline in that function (not a sudden loss).
3. The effect of NR in preserving motor action potential (FIG. 9) was observed.
4. Resveratrol showed no benefit (FIG. 1, and FIG. 2-FIG. 9).
5. The combination of NR and PT showed improved effect in comparison to the combination of NR and R. For example, as seen in FIG. 2, the survival in the NR+PT group is significantly higher than in the NR+R group. As seen in FIG. 4, the neurological score in the NR+PT group is significantly better than the control group (SOD1) and the NR+R group (which is essentially the same as the NR group). As seen in FIG. 5, in the rotarod experiment the NR+PT group is significantly better than the control group (SOD1) and the NR+R group.

Notably, in this experiment the results in the NR+R group are even worse than the ones shown for the NR group. Similar conclusions can be drawn from FIGS. 6, 7, and 8.

Incorporation by Reference

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Equivalents

Those skilled in the art will recognize, or be able to ascertain using no more than routine experimentation, many equivalents to the specific embodiments of the invention described herein. Such equivalents are intended to be encompassed by the following claims.

What is claimed is:

1. A method of treating or preventing amyotrophic lateral sclerosis (ALS) in a subject comprising administering to the subject a composition comprising pterostilbene and a compound of Formula I:

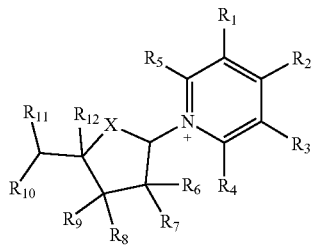

wherein, independently for each occurrence:
$R_1$, and $R_3$ are selected from hydrogen, halogen, —CN, —NO$_2$, —OR$_{14}$, —N(R$_{14}$)$_m$, —R$_{13}$, substituted or unsubstituted (C$_1$-C$_6$)alkyl, cycloalkyl, heterocycloalkyl, aryl, heteroaryl, aralkyl, and heteroaralkyl;
$R_4$ and $R_5$ are selected from hydrogen, halogen, —CN, —NO$_2$, —OR$_{14}$, —N(R$_{14}$)$_m$, substituted or unsubstituted (C$_1$-C$_6$)alkyl, cycloalkyl, heterocycloalkyl, aryl, heteroaryl, aralkyl, and heteroaralkyl;
$R_6$, $R_8$, $R_{11}$, and $R_{12}$ are selected from hydrogen, (C$_1$-C$_6$) alkyl, —((C$_1$-C$_6$)alkylene)N(R$_{14}$)$_m$, —C(O)((C$_1$-C$_6$) alkylene)N(R$_{14}$)$_m$, cycloalkyl, heterocycloalkyl, aryl, heteroaryl, aralkyl, heteroaralkyl, —OR$_{14}$, and —N(R$_{14}$)$_m$;
$R_7$, $R_9$, and $R_{10}$ are selected from —((C$_1$-C$_6$)alkylene)N (R$_{14}$)$_m$, —OR$_{14}$, and —N(R$_{14}$)$_m$;
$R_{13}$ is selected from —OR$_{14}$, —N(R$_{14}$)$_m$, —C(O)(R$_{14}$), —C(O)(OR$_{14}$), —C(O)N(R$_{14}$)$_m$, —S(O)$_2$(OR$_{14}$), —S(O)OR$_{14}$, and —S(O)$_2$N(R$_{14}$)$_m$;
$R_{14}$ is selected from hydrogen, (C$_1$-C$_6$)alkyl, cycloalkyl, heterocycloalkyl, aryl, heteroaryl, aralkyl, and heteroaralkyl; and
X is O, S, or N(R$_{14}$);
m is 2 or 3;
provided that at least one of $R_1$, $R_2$, and $R_3$ is $R_{13}$.

2. The method of claim 1, wherein the compound of Formula I is nicotinamide riboside.

3. A method of slowing or reversing the progression of amyotrophic lateral sclerosis (ALS) in a subject comprising administering to the subject a composition comprising pterostilbene and a compound of Formula I:

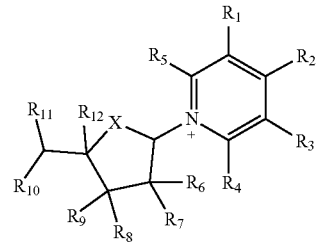

wherein, independently for each occurrence:
$R_1$, and $R_3$ are selected from hydrogen, halogen, —CN, —NO$_2$, —OR$_{14}$, —N(R$_{14}$)$_m$, —R$_{13}$, substituted or unsubstituted (C$_1$-C$_6$)alkyl, cycloalkyl, heterocycloalkyl, aryl, heteroaryl, aralkyl, and heteroaralkyl;
$R_4$ and $R_5$ are selected from hydrogen, halogen, —CN, —NO$_2$, —OR$_{14}$, —N(R$_{14}$)$_m$, substituted or unsubstituted (C$_1$-C$_6$)alkyl, cycloalkyl, heterocycloalkyl, aryl, heteroaryl, aralkyl, and heteroaralkyl;
$R_6$, $R_8$, $R_{11}$, and $R_{12}$ are selected from hydrogen, (C$_1$-C$_6$) alkyl, —((C$_1$-C$_6$)alkylene)N(R$_{14}$)$_m$, —C(O)((C$_1$-C$_6$) alkylene)N(R$_{14}$)$_m$, cycloalkyl, heterocycloalkyl, aryl, heteroaryl, aralkyl, heteroaralkyl, —OR$_{14}$, and —N(R$_{14}$)$_m$;
$R_7$, $R_9$, and $R_{10}$ are selected from —((C$_1$-C$_6$)alkylene)N (R$_{14}$)$_m$, —OR$_{14}$, and —N(R$_{14}$)$_m$;
$R_{13}$ is selected from —OR$_{14}$, —N(R$_{14}$)$_m$, —C(O)(R$_{14}$), —C(O)(OR$_{14}$), —C(O)N(R$_{14}$)$_m$, —S(O)$_2$(OR$_{14}$), —S(O)OR$_{14}$, and —S(O)$_2$N(R$_{14}$)$_m$;
$R_{14}$ is selected from hydrogen, (C$_1$-C$_6$)alkyl, cycloalkyl, heterocycloalkyl, aryl, heteroaryl, aralkyl, and heteroaralkyl; and
X is O, S, or N(R$_{14}$);
m is 2 or 3;
provided that at least one of $R_1$, $R_2$, and $R_3$ is $R_{13}$.

4. The method of claim 3, wherein the compound of Formula I is nicotinamide riboside.

5. The method of claim 1, wherein the method further comprising administering a fatty acid supplement to the subject.

6. The method of claim 5, wherein the fatty acid supplement is coconut oil.

7. The method of claim 1, wherein the administration of the composition comprises administering one or more doses of the composition.

8. The method of claim 7, wherein each dose of the composition comprises at least 40 mg of pterostilbene.

9. The method of claim 7, wherein each dose of the composition comprises at least 200 mg of nicotinamide riboside.

10. The method of claim 7, wherein ten or more doses of the composition are administered.

11. The method of claim 7, wherein the dose of the composition is administered at least once a week.

12. The method of claim 7, wherein the doses are administered for at least 7 days.

13. The method of claim 1, wherein the composition is administered orally.

14. The method of claim 1, wherein the method further comprises administering a motor function test.

15. The method of claim 14, wherein the motor function test is Revised Amyotrophic Lateral Sclerosis Functional Rating Scale (ALSFRS-R).

16. The method of claim 1, wherein the method further comprises administering a cognition and conduct function test selected from Complutense Verbal Learning Test (TAVEC), Symbol Digit Modalities Test (SDMT), Verbal Fluency Test, Digit Span (Wechsler Memory Scale III), D2 Attention Test, Wechsler Memory Scale III for Letters and Numbers, London Tower Test, Stroop test, Frontal System Behavior Scale (FrSBe), or Brief Test (subjective conduct).

17. The method of claim 1, wherein the method further comprises measuring a feature in the subject.

18. The method of claim 17, wherein the feature is associate with inflammation.

19. The method of claim 18, wherein the feature is the level of a cytokine, level of amyloid A protein, level of macrophage activation marker neopterin, level of creatine phosphokinase (CPK), level of erythrocyte sedimentation rate, level of C-reactive protein, plasma viscosity, or cell count.

20. The method of claim 19, wherein the cytokine is TNFa, IFNy, IL-1, IL-6, IL-8, or TGFβ.

\* \* \* \* \*